US010702392B2

(12) United States Patent
Greenhalgh et al.

(10) Patent No.: US 10,702,392 B2
(45) Date of Patent: *Jul. 7, 2020

(54) EXPANDABLE SUPPORT DEVICE AND METHOD OF USE

(71) Applicant: Theken Spine, LLC, Carlsbad, CA (US)

(72) Inventors: E. Skott Greenhalgh, Lower Gwynedd, PA (US); John-Paul Romano, Chalfont, PA (US)

(73) Assignee: Theken Spine, LLC, Carlsbad, CA (US)

( * ) Notice: Subject to any disclaimer, the term of this patent is extended or adjusted under 35 U.S.C. 154(b) by 448 days.

This patent is subject to a terminal disclaimer.

(21) Appl. No.: 15/488,956

(22) Filed: Apr. 17, 2017

(65) Prior Publication Data

US 2017/0216046 A1 Aug. 3, 2017

Related U.S. Application Data

(63) Continuation of application No. 13/870,584, filed on Apr. 25, 2013, now Pat. No. 9,622,876.

(60) Provisional application No. 61/638,148, filed on Apr. 25, 2012, provisional application No. 61/638,146, filed on Apr. 25, 2012.

(51) Int. Cl.
*A61F 2/44* (2006.01)
*A61B 17/88* (2006.01)
*A61F 2/30* (2006.01)
*A61F 2/46* (2006.01)

(52) U.S. Cl.
CPC .......... *A61F 2/447* (2013.01); *A61B 17/8852* (2013.01); *A61F 2/4425* (2013.01); *A61F 2/4455* (2013.01); *A61F 2/4611* (2013.01); *A61F 2002/30387* (2013.01); *A61F 2002/30405* (2013.01); *A61F 2002/30507* (2013.01); *A61F 2002/30556* (2013.01); *A61F 2002/30579* (2013.01); *A61F 2002/30904* (2013.01); *A61F 2002/443* (2013.01); *A61F 2002/448* (2013.01); *A61F 2002/4475* (2013.01); *A61F 2220/0025* (2013.01)

(58) Field of Classification Search
CPC .... A61F 2/4455–447; A61F 2002/4475; A61F 2002/448
See application file for complete search history.

(56) References Cited

U.S. PATENT DOCUMENTS

| | | |
|---|---|---|
| 4,863,476 A | 9/1989 | Shepperd |
| 5,609,635 A | 3/1997 | Michelson |
| 5,665,122 A | 9/1997 | Kambin |
| 5,776,199 A | 7/1998 | Michelson |
| 5,782,832 A | 7/1998 | Larsen et al. |
| 6,045,579 A | 4/2000 | Hochshuler et al. |
| 6,080,193 A | 6/2000 | Hochshuler et al. |
| 6,102,950 A | 8/2000 | Vaccaro |
| 6,129,763 A | 10/2000 | Brett |

(Continued)

*Primary Examiner* — Amy R Sipp
(74) *Attorney, Agent, or Firm* — Middleton Reutlinger

(57) ABSTRACT

An implantable orthopedic support device and methods of using the device are disclosed. The device can have rigid structural components that can translate longitudinally with respect to each other, and in so doing can change the vertical height of the device. The structural components can be driven by a drivescrew mechanism to change the vertical height of the device.

16 Claims, 19 Drawing Sheets

(56) References Cited

U.S. PATENT DOCUMENTS

| | | |
|---|---|---|
| 6,159,244 A | 12/2000 | Suddaby |
| 6,176,882 B1 | 1/2001 | Biedermann et al. |
| 6,183,517 B1 | 2/2001 | Suddaby |
| 6,193,757 B1 | 2/2001 | Foley et al. |
| 6,302,914 B1 | 10/2001 | Michelson |
| 6,332,895 B1 | 12/2001 | Suddaby |
| 6,371,989 B1 | 4/2002 | Chauvein et al. |
| 6,419,705 B1 | 7/2002 | Erickson |
| 6,436,140 B1 | 8/2002 | Liu et al. |
| 6,443,989 B1 | 9/2002 | Jackson |
| 6,447,544 B1 | 9/2002 | Michelson |
| 6,447,547 B1 | 9/2002 | Michelson |
| 6,454,807 B1 | 9/2002 | Jackson |
| 6,478,823 B1 | 11/2002 | Michelson |
| 6,488,710 B2 | 12/2002 | Besselink |
| 6,491,724 B1 | 12/2002 | Ferree |
| 6,562,074 B2 | 5/2003 | Gerbec et al. |
| 6,582,431 B1 | 6/2003 | Ray |
| 6,582,467 B1 | 6/2003 | Teitelbaum et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,706,070 B1 | 3/2004 | Wagner et al. |
| 6,723,126 B1 | 4/2004 | Berry |
| 6,733,535 B2 | 5/2004 | Michelson |
| 6,773,460 B2 | 8/2004 | Jackson |
| 6,852,129 B2 | 2/2005 | Gerbec et al. |
| 6,863,673 B2 | 3/2005 | Gerbec et al. |
| 6,866,682 B1 | 3/2005 | An et al. |
| 6,893,464 B2 | 5/2005 | Kiester |
| 6,953,477 B2 | 10/2005 | Berry |
| 6,955,691 B2 | 10/2005 | Chae et al. |
| 6,959,998 B2 | 11/2005 | Tsukamoto |
| 7,066,961 B2 | 6/2006 | Michelson |
| 7,087,055 B2 | 8/2006 | Lim et al. |
| 7,094,257 B2 | 8/2006 | Mujwid et al. |
| 7,118,579 B2 | 10/2006 | Michelson |
| 7,204,853 B2 | 4/2007 | Gordon et al. |
| 7,214,243 B2 | 5/2007 | Taylor |
| 7,217,293 B2 | 5/2007 | Branch |
| 7,311,713 B2 | 12/2007 | Johnson et al. |
| 7,316,714 B2 | 1/2008 | Gordon et al. |
| 7,384,431 B2 | 6/2008 | Berry |
| 7,431,735 B2 | 10/2008 | Liu et al. |
| 7,503,933 B2 | 3/2009 | Michelson |
| 7,507,241 B2 | 3/2009 | Levy et al. |
| 7,569,074 B2 | 8/2009 | Eisermann et al. |
| 7,575,601 B2 | 8/2009 | Dickson |
| 7,637,952 B2 | 12/2009 | Landry et al. |
| 7,655,043 B2 | 2/2010 | Peterman et al. |
| 7,655,046 B2 | 2/2010 | Dryer et al. |
| 7,674,296 B2 | 3/2010 | Rhoda et al. |
| 7,708,778 B2 | 5/2010 | Gordon et al. |
| 7,722,674 B1 | 5/2010 | Grotz |
| 7,731,751 B2 | 6/2010 | Butler et al. |
| 7,753,958 B2 | 7/2010 | Gordon et al. |
| 7,771,473 B2 | 8/2010 | Thramann |
| 7,785,351 B2 | 8/2010 | Gordon et al. |
| 7,789,914 B2 | 9/2010 | Michelson |
| 7,794,480 B2 | 9/2010 | Gordon et al. |
| 7,799,081 B2 | 9/2010 | McKinley |
| 7,799,082 B2 | 9/2010 | Gordon et al. |
| D626,233 S | 10/2010 | Cipoletti et al. |
| 7,819,921 B2 | 10/2010 | Grotz |
| 7,846,206 B2 | 12/2010 | Oglaza et al. |
| 7,862,618 B2 | 1/2011 | White et al. |
| 7,875,078 B2 | 1/2011 | Wysocki et al. |
| 7,887,596 B2 | 2/2011 | Douget et al. |
| 7,909,869 B2 | 3/2011 | Gordon et al. |
| 7,909,870 B2 | 3/2011 | Kraus |
| 7,914,581 B2 | 3/2011 | Dickson et al. |
| 7,918,889 B2 | 4/2011 | Vittur et al. |
| 7,922,729 B2 | 4/2011 | Michelson |
| 7,931,688 B2 | 4/2011 | Landry et al. |
| 7,967,866 B2 | 6/2011 | Dewey |
| 7,967,867 B2 | 6/2011 | Barreiro et al. |
| 7,976,579 B2 | 7/2011 | Francis |
| 7,981,157 B2 | 7/2011 | Castleman et al. |
| 8,002,831 B2 | 8/2011 | Burd et al. |
| 8,021,429 B2 | 9/2011 | Viker |
| 8,021,430 B2 | 9/2011 | Michelson |
| 8,025,665 B2 | 9/2011 | Lim et al. |
| 8,034,111 B2 | 10/2011 | Hsu et al. |
| 8,052,723 B2 | 11/2011 | Gordon et al. |
| 8,062,366 B2 | 11/2011 | Melkent |
| 8,062,368 B2 | 11/2011 | Heinz et al. |
| 8,062,372 B2 | 11/2011 | Tsuang et al. |
| 8,062,374 B2 | 11/2011 | Markworth et al. |
| 8,062,375 B2 | 11/2011 | Glerum et al. |
| 8,083,800 B2 | 12/2011 | Edie |
| 8,105,382 B2 | 1/2012 | Olmos et al. |
| 8,110,004 B2 | 2/2012 | Valdevit et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,137,401 B2 | 3/2012 | Stad et al. |
| 8,147,550 B2 | 4/2012 | Gordon et al. |
| 8,152,851 B2 | 4/2012 | Mueller et al. |
| 8,152,852 B2 | 4/2012 | Biyani |
| 8,172,903 B2 | 5/2012 | Gordon et al. |
| 8,182,538 B2 | 5/2012 | O'Neil et al. |
| 8,221,501 B2 | 7/2012 | Eisermann et al. |
| 8,241,294 B2 | 8/2012 | Sommerich et al. |
| 8,241,358 B2 | 8/2012 | Butler et al. |
| 8,241,363 B2 | 8/2012 | Sommerich et al. |
| 8,252,054 B2 | 8/2012 | Greenhalgh et al. |
| 8,257,440 B2 | 9/2012 | Gordon et al. |
| 8,303,658 B2 | 11/2012 | Peterman |
| 8,353,961 B2 | 1/2013 | McClintock et al. |
| 8,382,842 B2 | 2/2013 | Greenhalgh et al. |
| 8,382,843 B2 | 2/2013 | Laurence et al. |
| 8,403,990 B2 | 3/2013 | Dryer et al. |
| 8,409,282 B2 | 4/2013 | Kim |
| 8,435,299 B2 | 5/2013 | Chauvin et al. |
| 8,512,407 B2 | 8/2013 | Butler et al. |
| 8,535,380 B2 | 9/2013 | Greenhalgh et al. |
| 8,574,300 B2 | 11/2013 | McManus et al. |
| 8,585,761 B2 | 11/2013 | Theofilos |
| 8,585,763 B2 | 11/2013 | Olevsky et al. |
| 8,603,168 B2 | 12/2013 | Gordon et al. |
| 9,622,876 B1 * | 4/2017 | Greenhalgh ............ A61F 2/447 |
| 2003/0065396 A1 | 4/2003 | Michelson |
| 2003/0135279 A1 | 7/2003 | Michelson |
| 2005/0010292 A1 | 1/2005 | Carrasco |
| 2005/0080422 A1 | 4/2005 | Otte et al. |
| 2005/0125062 A1 | 6/2005 | Biedermann et al. |
| 2005/0273171 A1 | 12/2005 | Gordon et al. |
| 2005/0278036 A1 | 12/2005 | Leonard et al. |
| 2006/0122701 A1 | 6/2006 | Kiester |
| 2006/0129244 A1 | 6/2006 | Ensign |
| 2006/0195095 A1 | 8/2006 | Mueller et al. |
| 2006/0229729 A1 | 10/2006 | Gordon et al. |
| 2006/0241764 A1 | 10/2006 | Michelson |
| 2007/0032791 A1 | 2/2007 | Greenhalgh |
| 2007/0219634 A1 | 9/2007 | Greenhalgh et al. |
| 2007/0244485 A1 | 10/2007 | Greenhalgh et al. |
| 2007/0270968 A1 | 11/2007 | Baynham et al. |
| 2007/0288092 A1 | 12/2007 | Bambakidis |
| 2008/0021556 A1 | 1/2008 | Edie |
| 2008/0021559 A1 | 1/2008 | Thramann |
| 2008/0058931 A1 | 3/2008 | White et al. |
| 2008/0071356 A1 | 3/2008 | Greenhalgh et al. |
| 2008/0114454 A1 | 5/2008 | Peterman et al. |
| 2008/0147193 A1 | 6/2008 | Matthis et al. |
| 2008/0167657 A1 | 7/2008 | Greenhalgh |
| 2008/0183204 A1 | 7/2008 | Greenhalgh et al. |
| 2008/0281346 A1 | 11/2008 | Greenhalgh et al. |
| 2008/0288071 A1 | 11/2008 | Biyani et al. |
| 2008/0294206 A1 | 11/2008 | Greenhalgh et al. |
| 2008/0319549 A1 | 12/2008 | Greenhalgh et al. |
| 2009/0024204 A1 | 1/2009 | Greenhalgh et al. |
| 2009/0088788 A1 | 4/2009 | Mouw |
| 2009/0149956 A1 | 6/2009 | Greenhalgh et al. |
| 2009/0198338 A1 | 8/2009 | Phan |

(56) References Cited

U.S. PATENT DOCUMENTS

| | | |
|---|---|---|
| 2009/0216331 A1 | 8/2009 | Grotz et al. |
| 2009/0240335 A1 | 9/2009 | Arcenio et al. |
| 2009/0281625 A1 | 11/2009 | Enayati |
| 2010/0063510 A1 | 3/2010 | Ariet et al. |
| 2010/0070036 A1 | 3/2010 | Implicito |
| 2010/0070041 A1 | 3/2010 | Peterman et al. |
| 2010/0082109 A1 | 4/2010 | Greenhalgh et al. |
| 2010/0087924 A1 | 4/2010 | Ariet |
| 2010/0179594 A1 | 7/2010 | Theofilos et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0217325 A1 | 8/2010 | Hochschuler et al. |
| 2010/0222884 A1 | 9/2010 | Greenhalgh |
| 2010/0234952 A1 | 9/2010 | Peterman |
| 2010/0286692 A1 | 11/2010 | Greenhalgh et al. |
| 2010/0286780 A1 | 11/2010 | Dryer et al. |
| 2010/0331985 A1 | 12/2010 | Gordon et al. |
| 2011/0077742 A1 | 3/2011 | White et al. |
| 2011/0093074 A1 * | 4/2011 | Glerum ............... A61F 2/447 623/17.16 |
| 2011/0130835 A1 | 6/2011 | Ashley et al. |
| 2011/0144753 A1 | 6/2011 | Marchek et al. |
| 2011/0172774 A1 | 7/2011 | Varela |
| 2011/0202135 A1 | 8/2011 | Baek et al. |
| 2011/0208312 A1 | 8/2011 | Moskowitz et al. |
| 2011/0218572 A1 | 9/2011 | Lechmann et al. |
| 2011/0276139 A1 | 11/2011 | Mahoney et al. |
| 2011/0319995 A1 | 12/2011 | Voellmicke et al. |
| 2011/0319997 A1 | 12/2011 | Glerum et al. |
| 2011/0320000 A1 | 12/2011 | O'Neil et al. |
| 2012/0004726 A1 | 1/2012 | Greenhalgh et al. |
| 2012/0059475 A1 | 3/2012 | Weiman |
| 2012/0226357 A1 | 9/2012 | Varela |
| 2013/0006361 A1 | 1/2013 | Glerum et al. |

\* cited by examiner

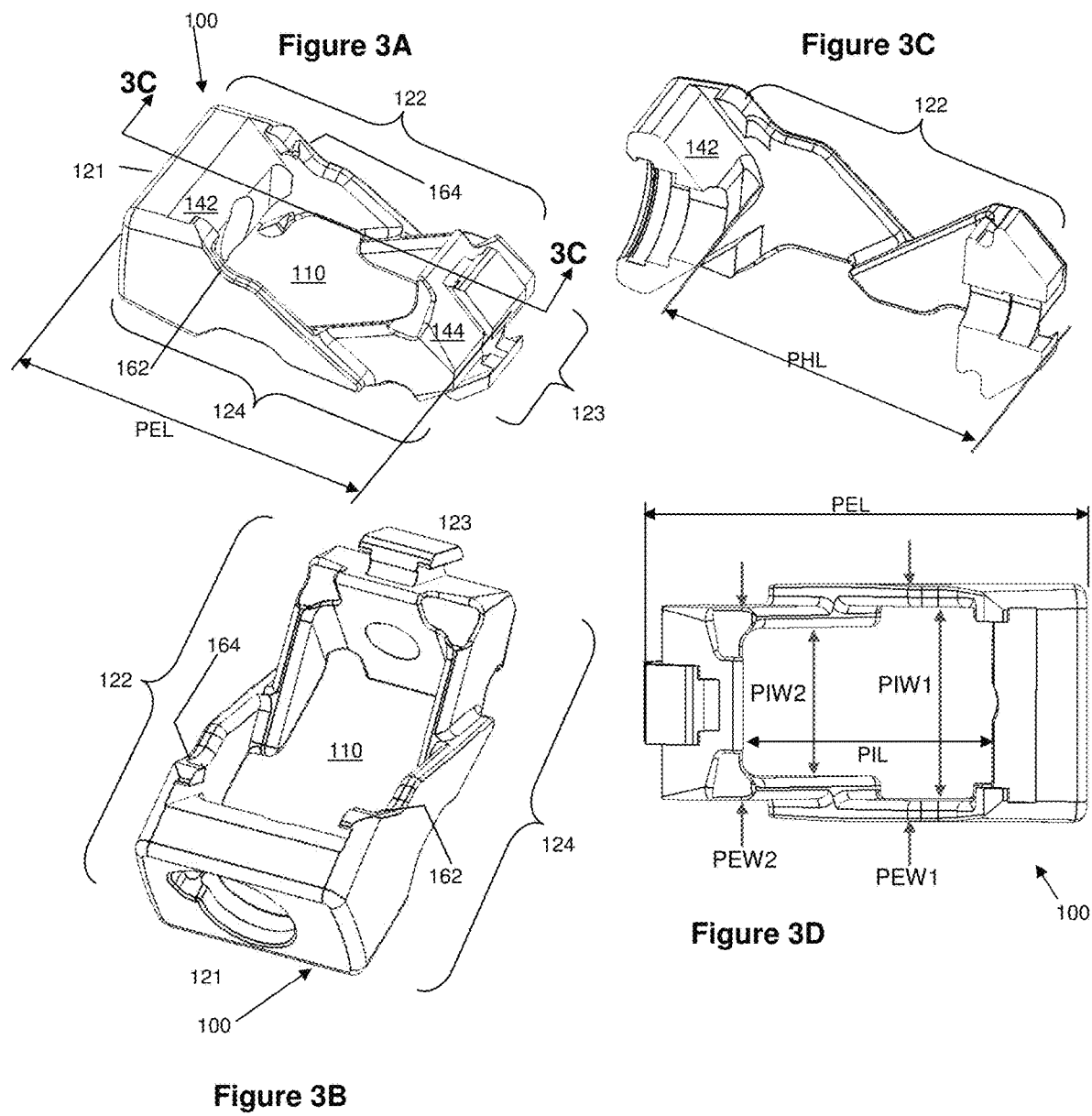

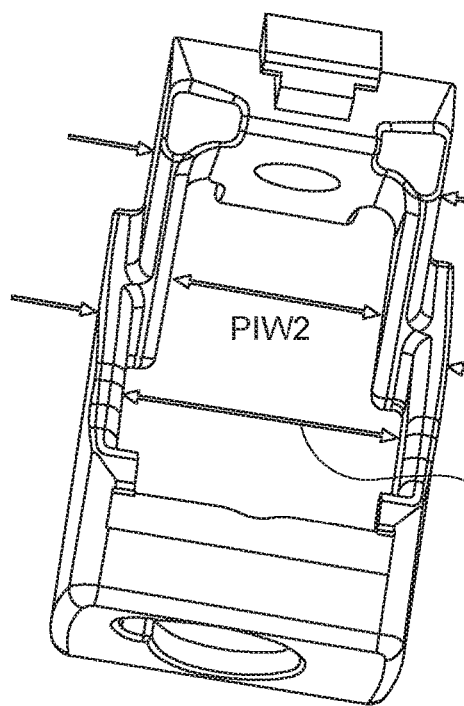
Figure 3E
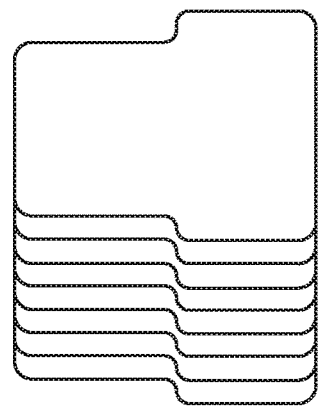
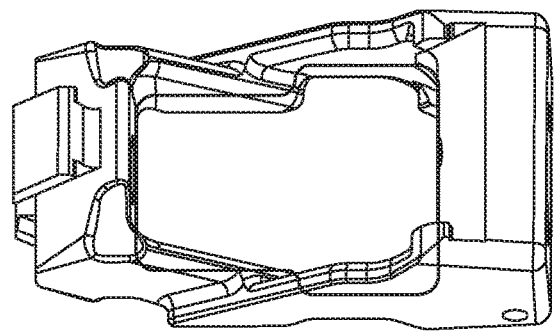
Figure 4
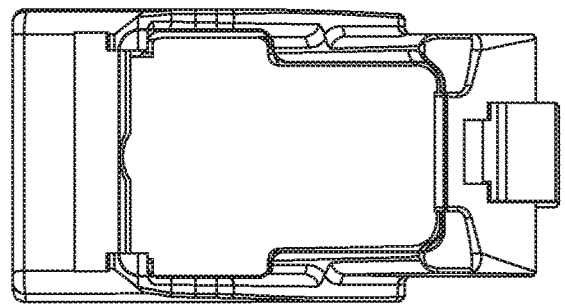

Smaller internal dimension

Larger internal dimension

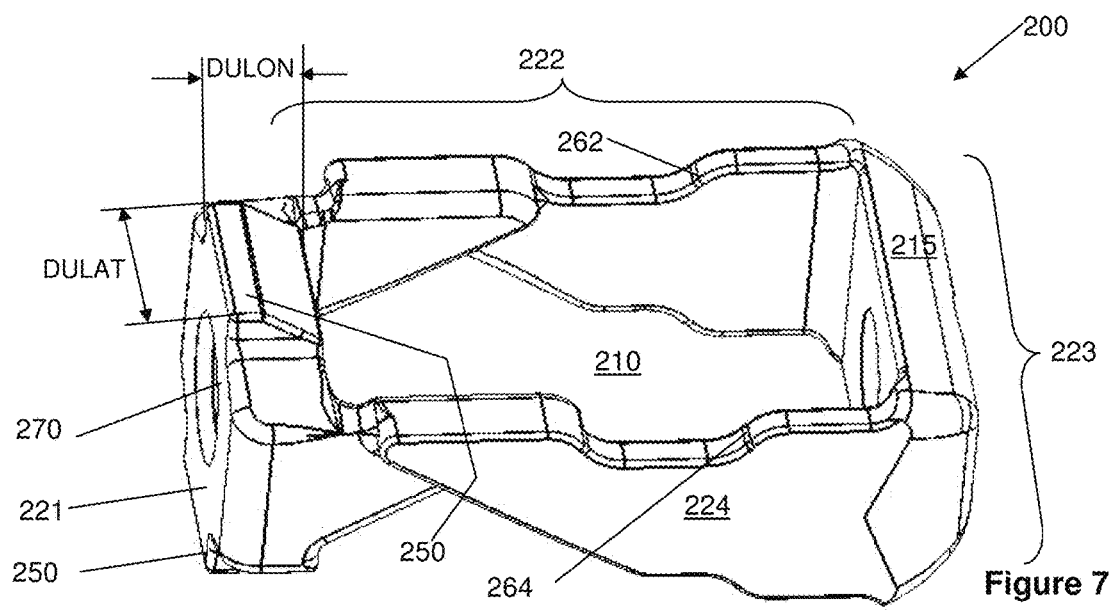
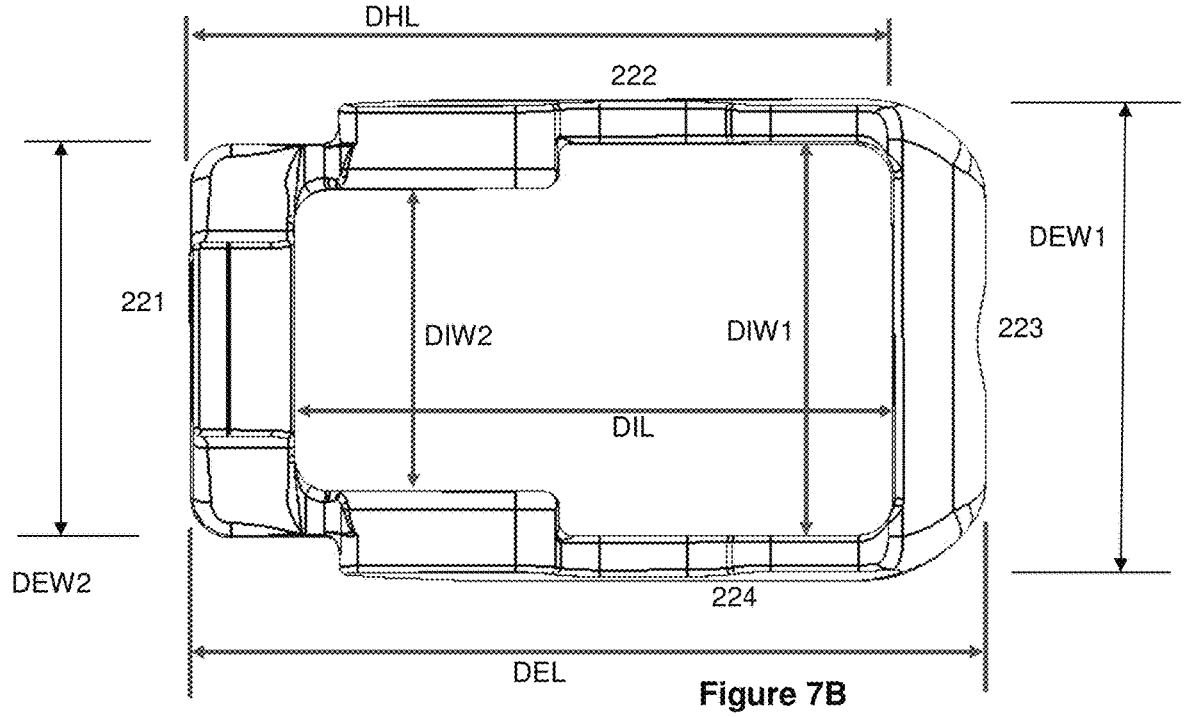

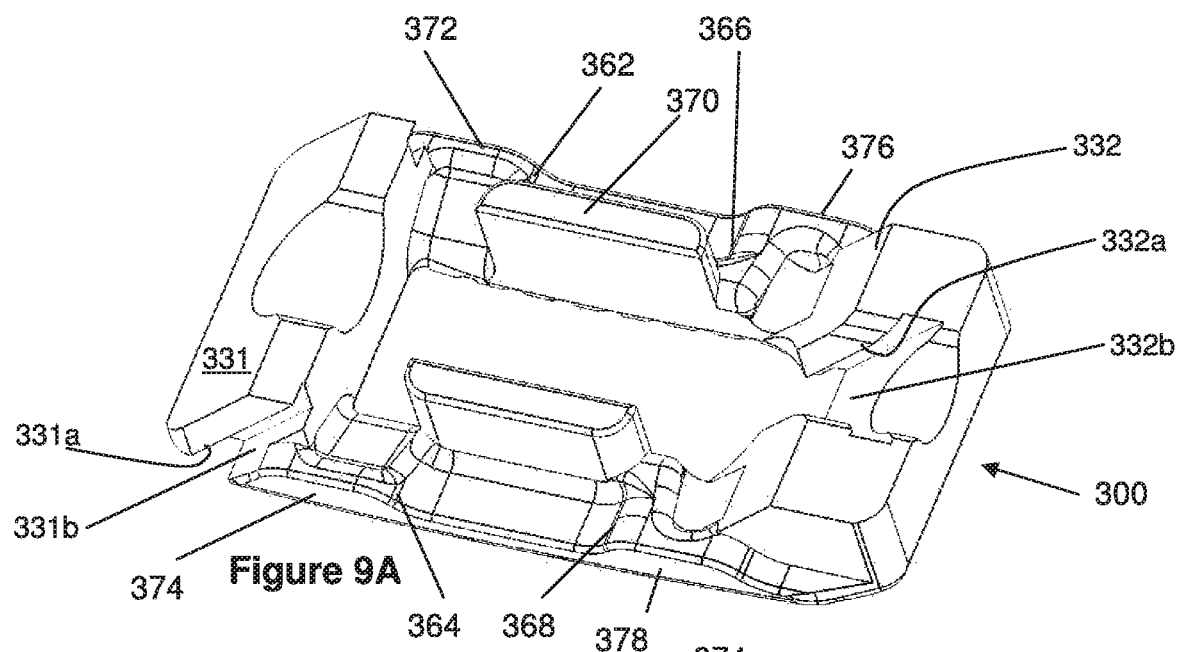
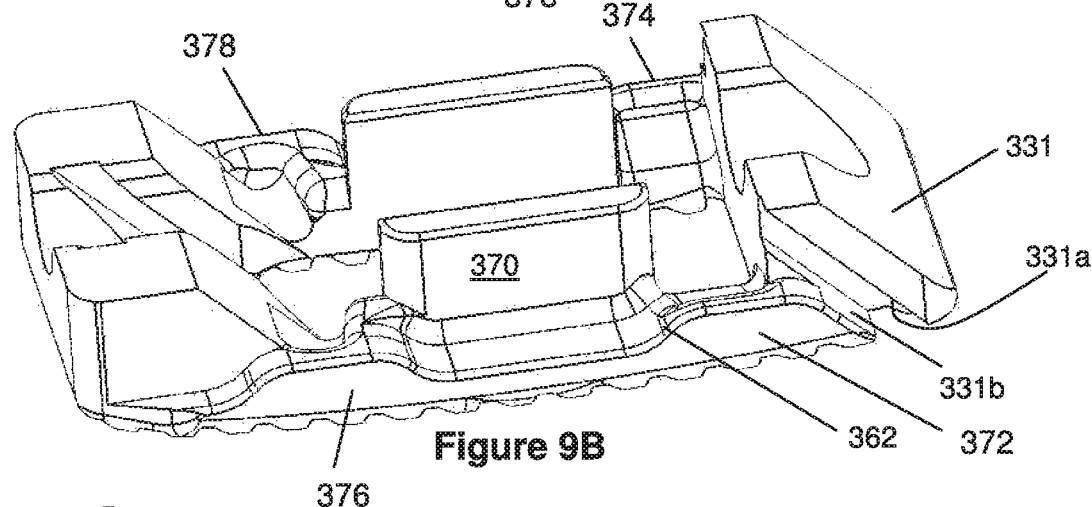
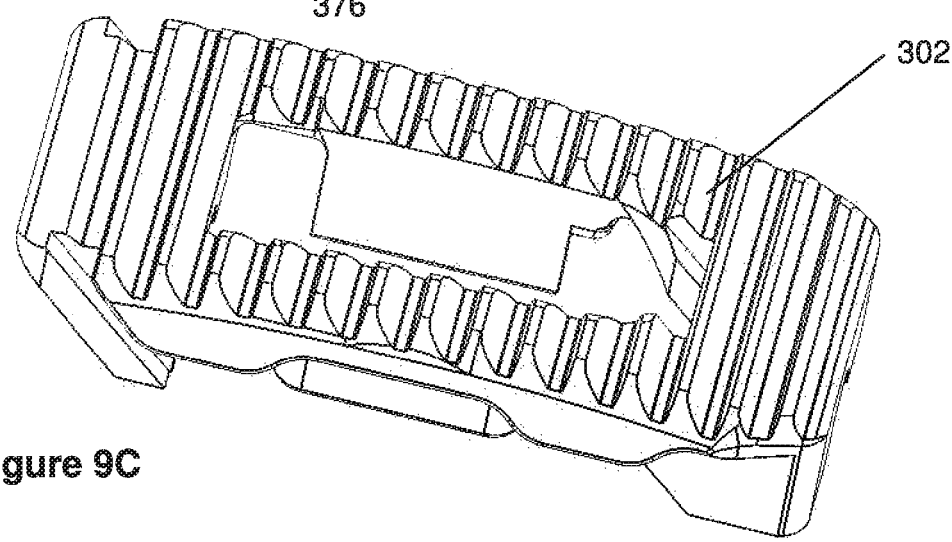
Figure 9A
Figure 9B
Figure 9C

External lateral dimension of pair of stability bars

Internal lateral dimension ring structure

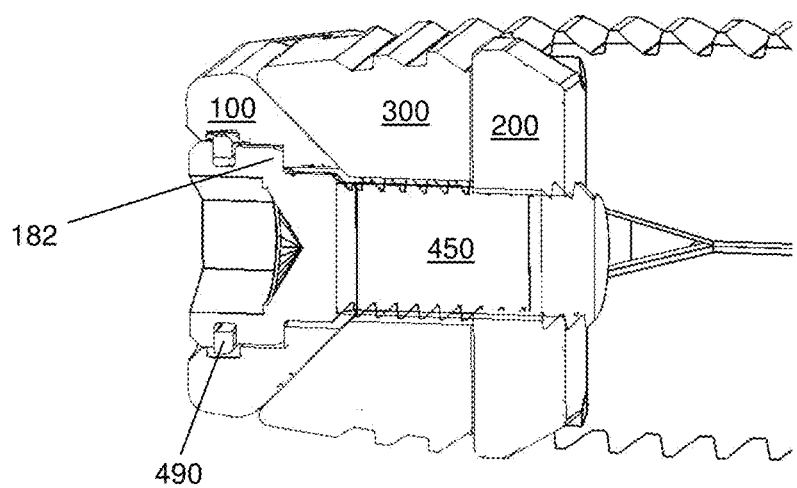
Figure 14A
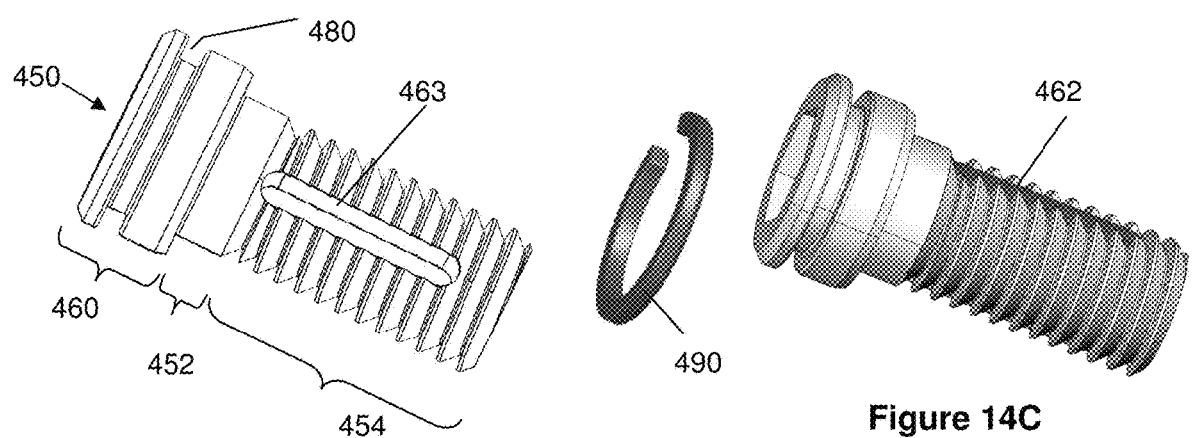
Figure 14B
Figure 14C
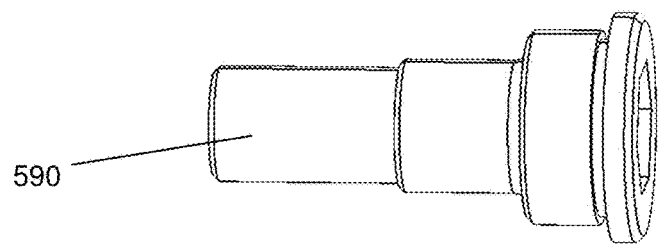
Figure 14D

EXPANDABLE SUPPORT DEVICE AND METHOD OF USE

CROSS-REFERENCE TO RELATED APPLICATIONS

This application is a continuation of, and claims priority to and benefit under 35 U.S.C. § 120 to copending U.S. application Ser. No. 13/870,584, filed Apr. 25, 2013, which claims priority to and benefit under 35 U.S.C. § 119(e) to U.S. Provisional Application No. 61/638,148, filed Apr. 25, 2012, and U.S. Provisional Application No. 61/638,146, filed Apr. 25, 2012, the entire contents of which are hereby incorporated by reference.

BACKGROUND

1. Technical Field

Devices and methods for fixation of tissue are disclosed. More specifically, the devices and methods can be for interbody vertebral fusion of vertebrae or for fusion of other bones to one another.

2. Background of the Art

There already exist many intervertebral spacers of fixed dimensions. There are also some expandable intervertebral spacers, which allow insertion through a relatively small surgical incision, followed by expansion of the device once it is in position at the surgical site. However, there is still a need for improved expandable spacers.

SUMMARY OF THE INVENTION

Embodiments of the invention may generally comprise a central mechanism that comprises a proximal ring structure and a distal ring structure. The proximal ring structure and the distal ring structure may be able to translate relative to each other. At least one or both of the proximal ring structure and the distal ring structure may comprise ramps. Ramps may be any combination of interlocking and non-interlocking. Embodiments of the invention may further comprise endplates, which may be able to move vertically toward or away from each other in response to relative translational motion of the proximal ring structure and the distal ring structure, and which may comprise ramps that are complementary to ramps in the ring structures.

In an embodiment of the invention, there may be provided an implantable device having a central mechanism comprising a proximal ring structure and a distal ring structure, in which one of the ring structures has four sides, and of those four sides, two opposed sides have offsets such that there can be defined a first inside width and a second inside width and a first outside width and a second outside width, wherein the smaller of the outside widths is less than the larger of the inside widths.

In an embodiment of the invention, there may be provided an implantable device having a central mechanism comprising a proximal ring structure and a distal ring structure, in which at least one of the ring structures has a central opening that has a first internal width dimension and a second internal width dimension, wherein the first internal width dimension is different from the second internal width dimension.

In an embodiment of the invention, there may be provided an implantable device having a central mechanism comprising a proximal ring structure and a distal ring structure, in which the proximal ring structure has a first ramp and a second ramp, in which the first ramp comprises a receiving structure capable of engaging a first complementary shape, and the second ramp comprises a protruding shape capable of engaging a second complementary shape.

In an embodiment of the invention, there may be provided an implantable device having a central mechanism comprising a proximal ring structure and a distal ring structure, in which the proximal ring structure has a first ramp that extends continuously across the centerplane, and in which the proximal ring structure also has two additional ramps, one on each side of the centerplane, and not intersecting the centerplane, with the two additional ramps being coplanar with each other.

In an embodiment of the invention, there may be provided an implantable device having a central mechanism comprising a proximal ring structure and a distal ring structure, in which the proximal ring structure has a plurality of ramps, in which at least one of the ramps has an engagement feature and another of the ramps does not have an engagement feature. An engagement feature may be either a protrusion or a receiver, and may be either interlocking or non-interlocking.

In an embodiment of the invention, there may be provided an implantable device having a central mechanism comprising a proximal ring structure and a distal ring structure, in which the proximal ring structure has a three different outward-facing ramp surfaces, in which the three different outward-facing ramp surfaces are parallel with each other but are located in three different non-coplanar planes.

In an embodiment of the invention, there may be provided an implantable device having a central mechanism comprising a proximal ring structure and a distal ring structure, in which the proximal ring structure has a plurality of outward-facing ramps, such that each ramp has a respective ramp width, measured in a lateral direction, of whatever portion of the ramp surface is planar, wherein the widths of different ramps are unequal.

In an embodiment of the invention, there may be provided an implantable device having a central mechanism comprising a proximal ring structure and a distal ring structure, wherein the distal ring structure comprises a vertically extending urging structure and a transition between the urging structure and the distal ring structure.

In an embodiment of the invention, there may be provided an implantable device having a central mechanism comprising a proximal ring structure and a distal ring structure, wherein the distal ring structure has a smallest internal width in a lateral direction and has a vertically extending urging structure having an urging structure width in a lateral direction, wherein the urging structure width is less than the smallest internal width of the distal ring structure.

In an embodiment of the invention, there may be provided an implantable device having a central mechanism comprising a proximal ring structure and a distal ring structure, wherein the proximal ring structure and a distal ring structure, when viewed along a vertical direction, partially but not completely overlap with each other.

In an embodiment of the invention, there may be provided an implantable device having a central mechanism comprising a proximal ring structure and a distal ring structure, wherein at some place the proximal ring structure has an external lateral dimension smaller than a corresponding internal lateral dimension of the distal ring structure, and in another place, the distal ring structure has an external lateral dimension smaller than a corresponding internal lateral dimension of the proximal ring structure.

In an embodiment of the invention, there may be provided an implantable device having a central mechanism comprising a proximal ring structure and a distal ring structure, wherein, in all permitted positions of the distal ring structure relative to the proximal ring structure, in a section of the device taken along a longitudinal direction, there is a first end of the proximal ring structure, followed by a first end of the distal ring structure, followed by a second end of the proximal ring structure, followed by a second end of the distal ring structure.

In an embodiment of the invention, there may be provided an implantable device having a central mechanism comprising a proximal ring structure and a distal ring structure, wherein, in some cross-section taken in a first plane perpendicular to a longitudinal direction, there is in sequence progressing in a lateral direction the proximal ring structure followed by the distal ring structure followed by some empty space followed by the distal ring structure followed by the proximal ring structure, and wherein, in some other cross-section taken in a second plane perpendicular to the longitudinal direction, there is in sequence progressing in a lateral direction, the distal ring structure followed by the proximal ring structure followed by some empty space followed by the proximal ring structure followed by the distal ring structure.

In an embodiment of the invention, there may be provided an implantable device having a central mechanism comprising a proximal ring structure and a distal ring structure, wherein the device has a central opening therethrough generally along a vertical direction, and wherein the central opening is bounded in sequence around its perimeter by a first end, a first side, a second end and a second side, wherein in the sequence, is bounded on the first end by the proximal ring structure; then, on the first side adjacent to the first end, is bounded first by the proximal ring structure and then by the distal ring structure; then, on the second end is bounded by the distal ring structure; then, on the second side, is bounded first by the distal ring structure and then by the proximal ring structure.

In an embodiment of the invention, there may be provided an implantable device having a central mechanism and an endplate, wherein the endplate has a central hole through the outward-facing surface and generally through the endplate, and wherein the central opening has a dimension in a lateral direction and the endplate has a pair of stability bars depending therefrom away from the outward-facing surface, the stability bars having parallel surfaces facing toward each other defining a distance therebetween in the lateral direction, and wherein the distance between the stability bars equals the central hole lateral dimension.

In an embodiment of the invention, there may be provided an implantable device having a central mechanism and an endplate, wherein the endplate comprises a first ramp comprising a protruding structure capable of engaging a first complementary shape, and comprises a second ramp comprising a receiving shape capable of engaging a second complementary shape.

In an embodiment of the invention, there may be provided an implantable device having a central mechanism and an endplate, wherein the endplate comprises a first outward-facing ramp straddling both sides of a centerplane of the endplate, and further comprises further comprises a distinct separate outward-facing side ramp located so as not to intersect the centerplane of the endplate.

In an embodiment of the invention, there may be provided an implantable device having a central mechanism and an endplate, wherein the endplate comprises a first outward-facing ramp surface that has an engagement feature and a second outward-facing ramp surface that does not have an engagement feature. An engagement feature may be either a protrusion or a receiver, and may be either interlocking or non-interlocking.

In an embodiment of the invention, there may be provided an implantable device having a central mechanism and an endplate, wherein the endplate comprises a first outward-facing ramp surface and a second outward-facing ramp surface and a third outward-facing ramp surface, wherein the first, second and third outward-facing ramp surfaces lie in different planes and are parallel to each other.

In an embodiment of the invention, there may be provided an implantable device having a central mechanism and an endplate, wherein the endplate comprises a first outward-facing ramp surface and a second outward-facing ramp surface, wherein the first and second ramp surfaces are of unequal widths.

In an embodiment of the invention, there may be provided an implantable device having a central mechanism and an endplate, wherein the endplate comprises a ramp surface and also has a central hole therethrough, wherein the ramp intersects an edge of the central hole.

In an embodiment of the invention, there may be provided an implantable device having a central mechanism comprising a proximal ring structure and a distal ring structure, and comprising an endplate, wherein the endplate comprises stability bar depending therefrom, wherein the stability bars are inside the proximal ring structure and inside the distal ring structure.

In an embodiment of the invention, there may be provided an implantable device having a central mechanism comprising a proximal ring structure and a distal ring structure, wherein the distal ring structure has a vertically extending urging structure having an urging structure width in a lateral direction, and an endplate that is engaged with but movable with respect to the central mechanism, the endplate having a central hole having a central hole width in a lateral direction, wherein the urging structure width is less than the central hole width.

In an embodiment of the invention, there may be provided an implantable device having a central mechanism comprising a proximal ring structure and a distal ring structure, and comprising an endplate having a central hole therethrough and having a stability bar depending from the endplate, wherein the distal ring structure has an urging structure, wherein, in a longitudinal direction, the urging structure fits between the central hole internal wall and the stability bar.

In an embodiment of the invention, there may be provided an implantable device having a central mechanism comprising a proximal ring structure and a distal ring structure, and comprising an endplate, wherein the endplate has a pair of stability bars depending therefrom away from the outward-facing surface and has a pair of overhanging guides depending therefrom away from the outward-facing surface, and wherein the overhanging guides are more laterally outward than the stability bars.

In an embodiment of the invention, there may be provided an implantable device having a central mechanism comprising a first structure and a second structure, and comprising an endplate, having a central hole therethrough having an internal perimeter surface, wherein, in at least one direction of motion, the urging structure bears against the internal perimeter surface of the central opening of the endplate.

In an embodiment of the invention, there may be provided an implantable device having a central mechanism comprising a first structure and a second structure, and comprising an endplate, having a central hole therethrough having an internal perimeter surface, wherein, in at least one direction of motion, the urging surface bears against an external surface of the stability bar of the endplate.

In an embodiment of the invention, there may be provided an implantable device having a central mechanism comprising a first structure and a second structure able to undergo relative translation with respect to each other, with at least one of the structures having a driving ramp having an interlocking feature, and comprising an endplate having an endplate ramp complementary to the driving ramp and to its interlocking feature, and comprising a drive means, wherein translation of the central mechanism in one direction drives the endplate away from the central mechanism and translation of the central mechanism in the opposite direction drives the endplate toward the central mechanism, and wherein the central mechanism has a central opening therethrough and the drive means does not cross the central opening.

In an embodiment of the invention, there may be provided an implantable device having a central mechanism comprising a proximal ring structure and a distal ring structure, and wherein the relative motion of the endplate relative to the proximal ring structure may be caused by an urging structure of the distal ring structure pushing on the endplate close to a first ramp, and relative motion of the endplate relative to the proximal ring structure may also or alternatively be caused by a surface of a distally located portion of the distal ring structure pushing on a distal surface of the endplate.

In an embodiment of the invention, there may be provided an implantable device having a central mechanism comprising a proximal ring structure and a distal ring structure, wherein the proximal ring structure and the distal ring structure are connected by a guide means and also by a drive means, and wherein both the drive means and the guide means have respective central holes therethrough suitable to receive a K-wire.

In an embodiment of the invention, there may be provided an implantable device having a central mechanism comprising a proximal ring structure and a distal ring structure, wherein the proximal ring structure and the distal ring structure are connected by a guide means and also by a drive means comprising a drivescrew, and wherein the drivescrew engages complementary threads in the distal ring structure, and the drivescrew comprises a polymeric material that creates a mechanical interference to bear against the threads.

In an embodiment of the invention, there may be provided an implantable device having a central mechanism comprising a proximal ring structure and a distal ring structure, wherein the proximal ring structure and the distal ring structure are connected by a drive means comprising a drivescrew, wherein the drivescrew also comprises a circumferential groove that may accept a snap-ring.

In an embodiment of the invention, there may be provided an implantable device having a central mechanism comprising a first structure and a second structure, wherein the first structure and the second structure are connected by a drive means comprising a drivescrew, wherein the drivescrew comprises a head groove and one of the structures comprises a circumferential internal groove, and further comprising a snap-ring that partially occupies the head groove and partially occupies the circumferential internal groove.

BRIEF DESCRIPTION OF THE ILLUSTRATIONS

FIG. 3A is a three-dimensional view of the proximal ring structure. FIG. 3B is similar to FIG. 3A except from a different vantage point. FIG. 3C is a three-dimensional view of a section of the proximal ring structure taken along line 3C-3C of FIG. 3A. FIG. 3D is a top view of the proximal ring structure. FIG. 3E is a three-dimensional view of the proximal ring structure, nearly from the top, with certain dimensions defined.

FIG. 4 is an illustration showing the proximal ring structure in a top view, along with a view that is three-dimensional but nearly a top view, and along with a repeated shape of its central opening, all in order to describe the central opening of the proximal ring structure.

Figure 5A:
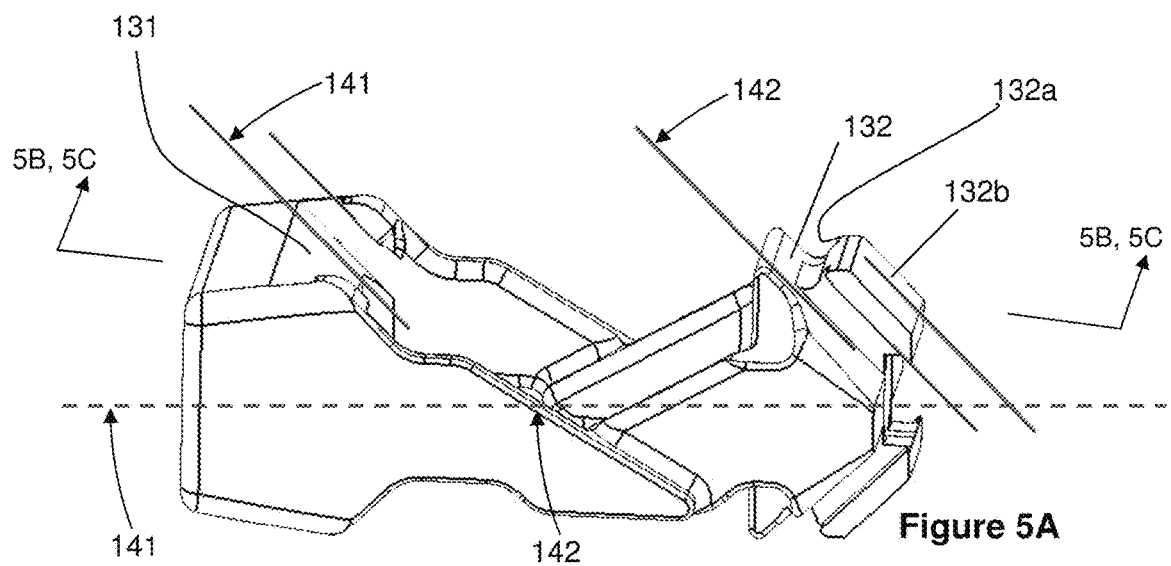
Figure 5B:
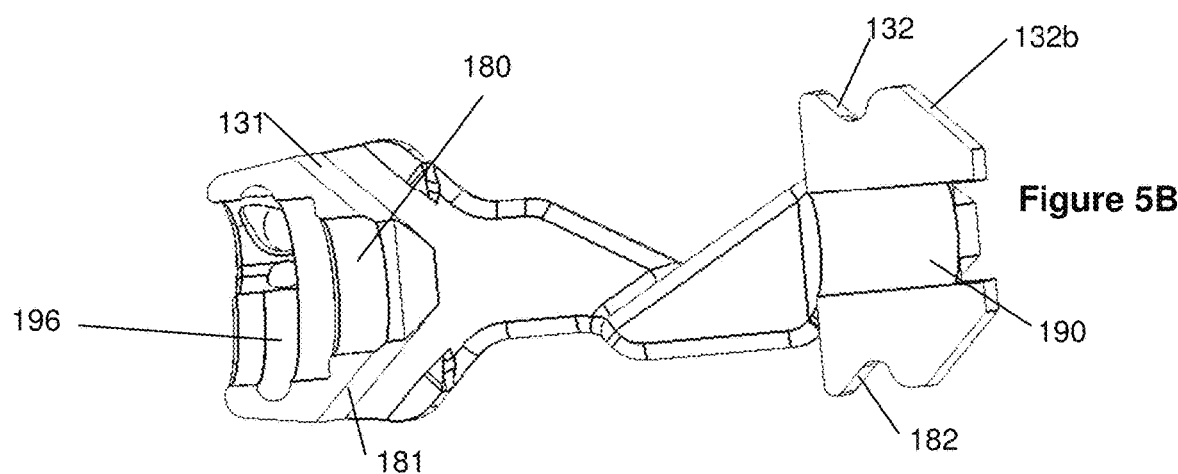
Figure 5C:
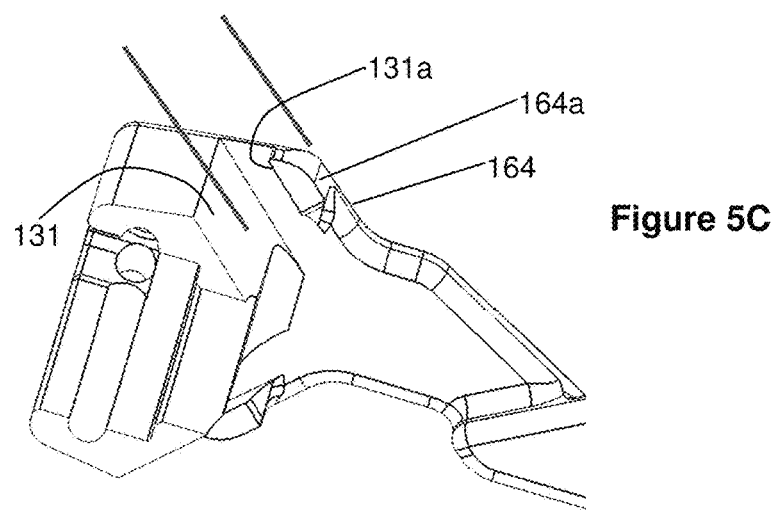

FIG. 5A is another three-dimensional view of the proximal ring structure, three-dimensionally but somewhat from the side. FIG. 5B is a view of a section of the proximal ring structure taken along line 5B-5B of FIG. 5A, nearly from a side. FIG. 5C is a more close-up three-dimensional view of some of a section of the proximal ring structure taken along line 5C-5C of FIG. 5A.

Figure 6A:
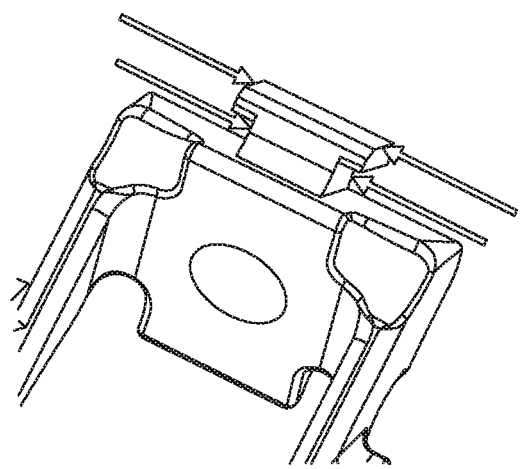
Figure 6B:
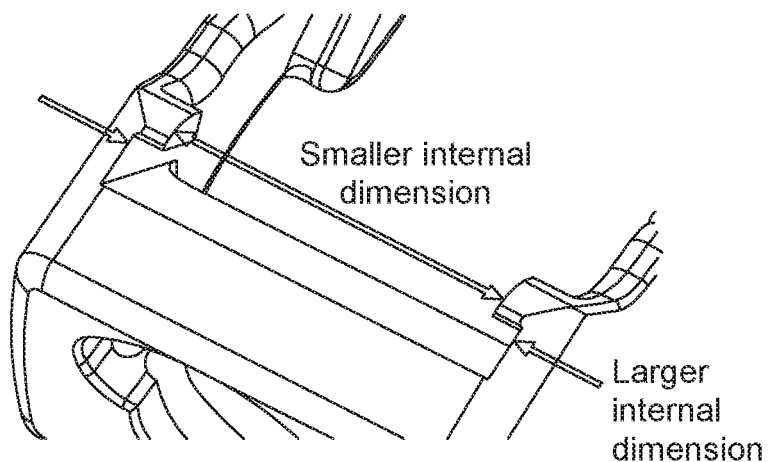
Figure 6C:
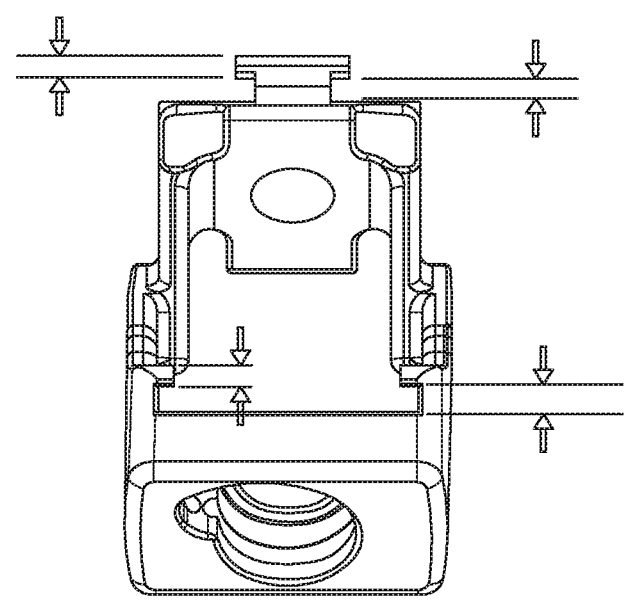

FIG. 6A is a three-dimensional view of a portion of the proximal ring structure, defining certain dimensions. FIG. 6B is a three-dimensional view of another portion of the proximal ring structure, defining certain other dimensions. FIG. 6C is a three-dimensional view of the proximal ring structure, defining certain dimensions.

Figure 7C:
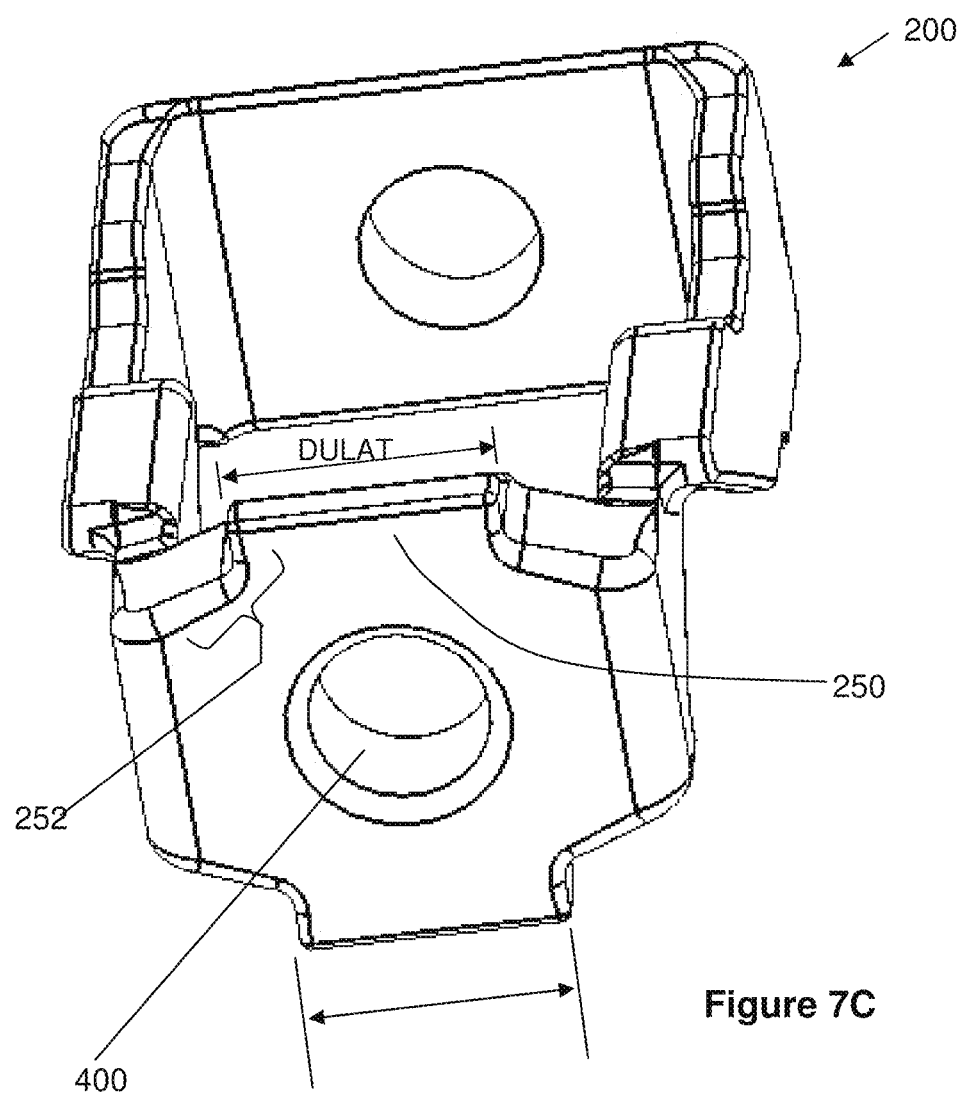

FIG. 7A is a three-dimensional view of the distal ring structure. FIG. 7B is a top view of the distal ring structure. FIG. 7C is a three-dimensional view of the distal ring structure somewhat from an end.

Figure 8A:
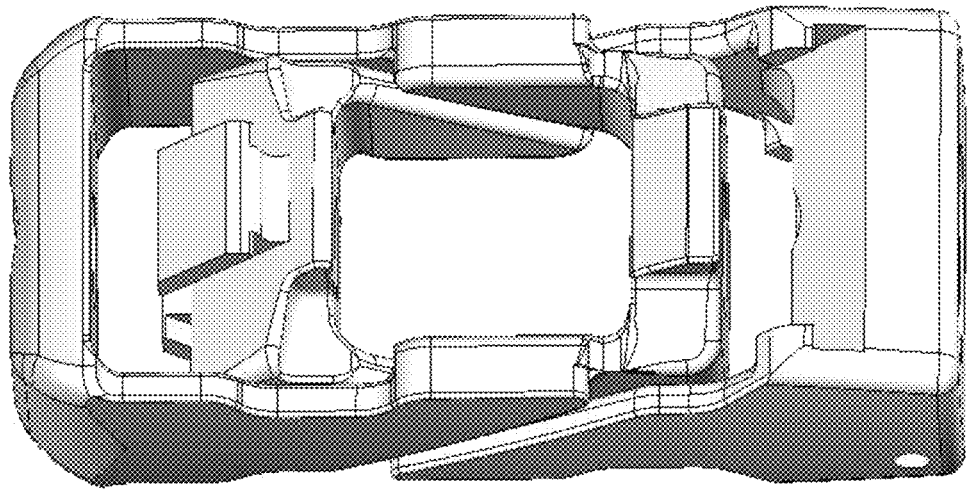
Figure 8B:
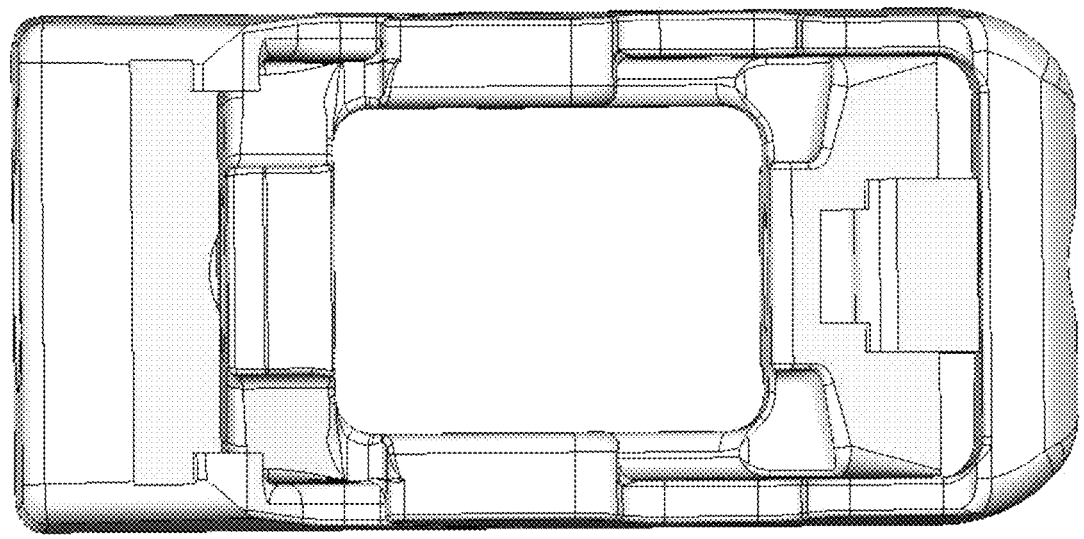
Figure 8C:
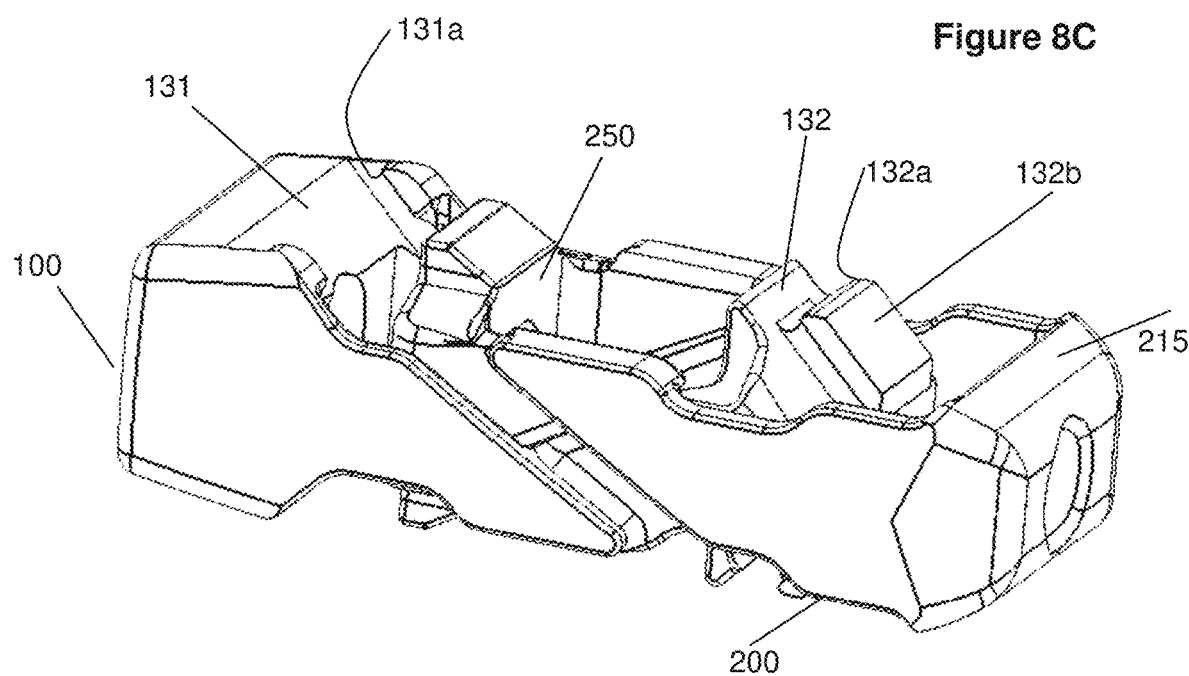
Figure 8D:
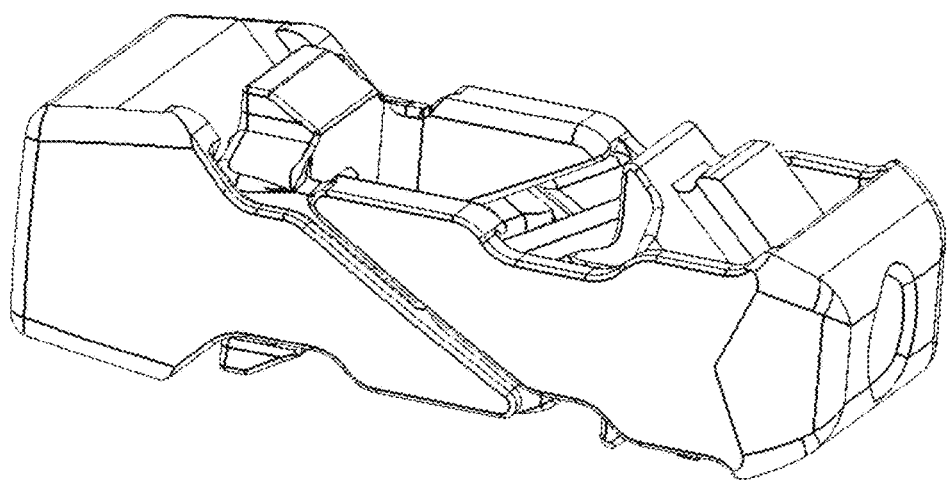

FIG. 8A is a three-dimensional view of a subassembly of the proximal ring structure and the distal ring structure. FIG. 8B is a top view of the same. FIG. 8C is another three-dimensional view of the same, from a different perspective, with the two ring structures positioned relative to each other in what would be the vertically contracted configuration of the overall device. FIG. 8D is similar to FIG. 8C, but with the two ring structures positioned relative to each other in what would be the vertically expanded configuration of the overall device.

Figure 9D:
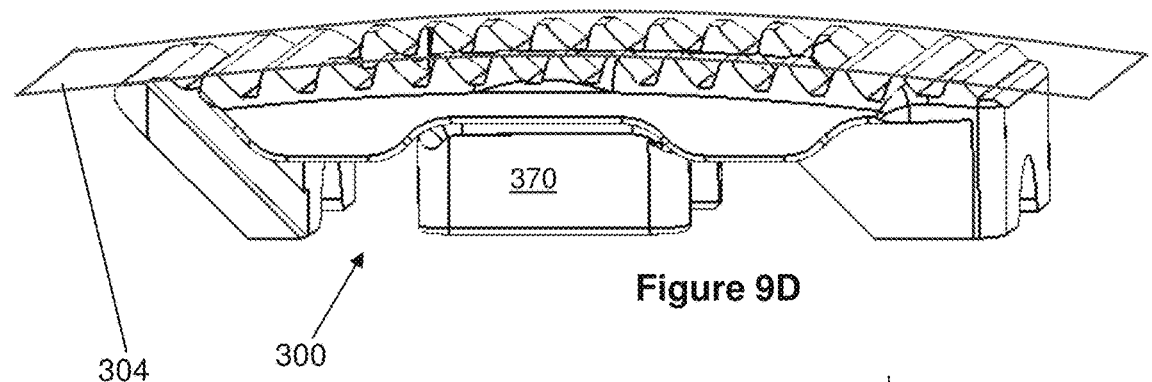
Figure 9E:
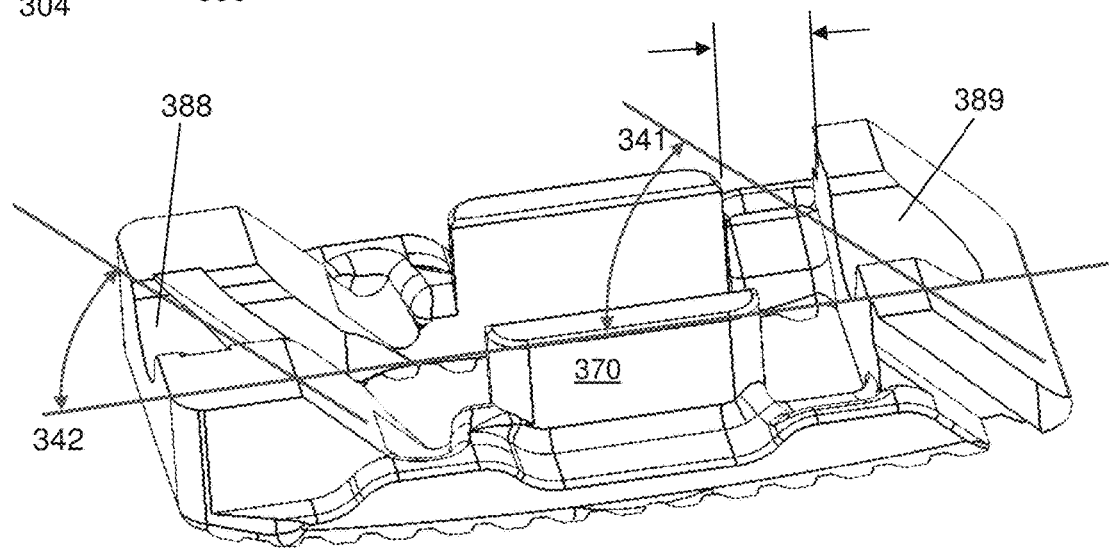
Figure 9F:
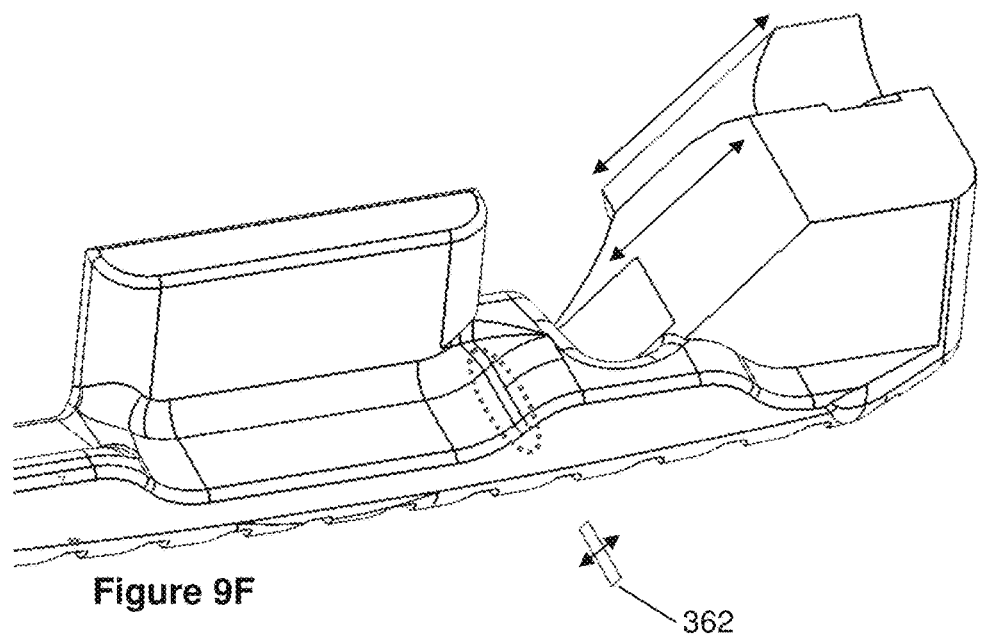
Figure 9G:
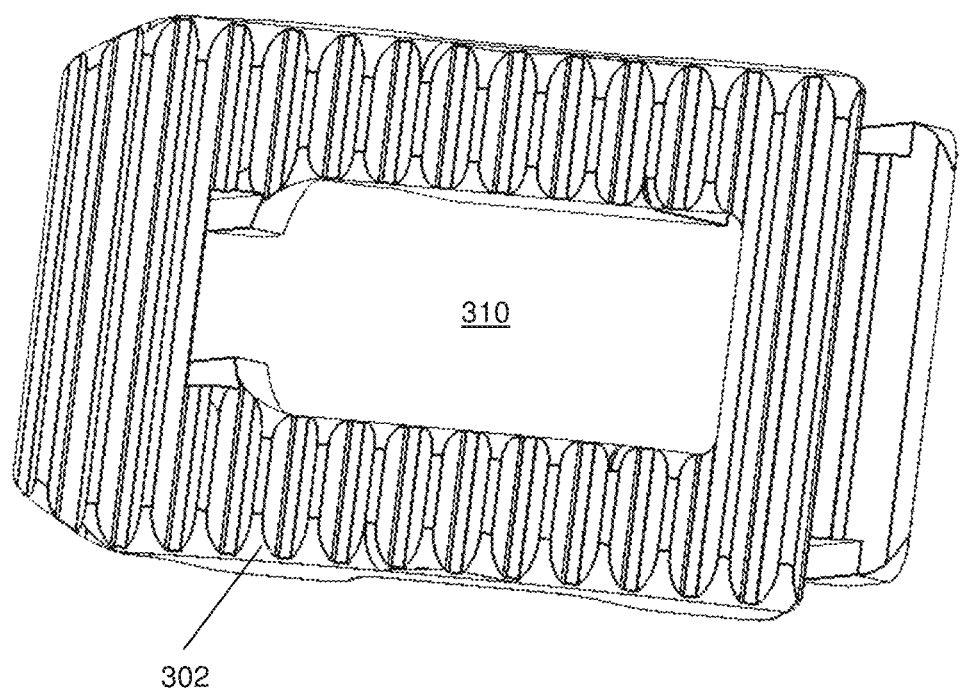

FIG. 9A is a three-dimensional view of an endplate, looking somewhat at a surface of the endplate that would face internally in the assembled device. FIG. 9B is a similar three-dimensional view of an endplate, from a different perspective. FIG. 9C is a three-dimensional view of the endplate looking at a surface of the endplate that would face externally in the assembled device. FIG. 9D is similar to FIG. 9C but viewed more from a side. FIG. 9E is a three-dimensional view of the endplate with certain ramp angles defined. FIG. 9F is another three-dimensional view of the endplate. FIG. 9G is a view of the endplate showing especially the external (bone-facing) surface of the endplate.

Figure 10A:
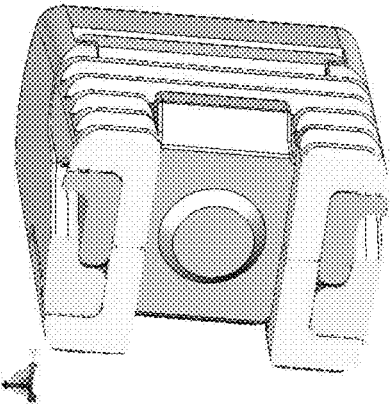
Figure 10B:
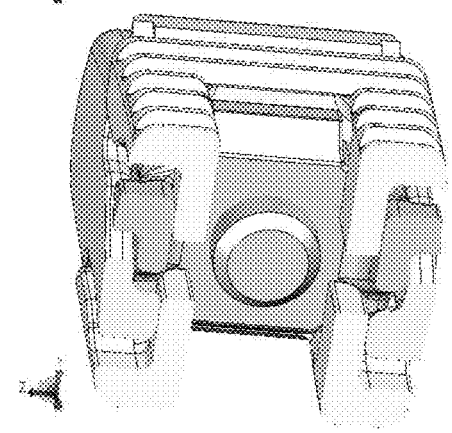
Figure 10C:
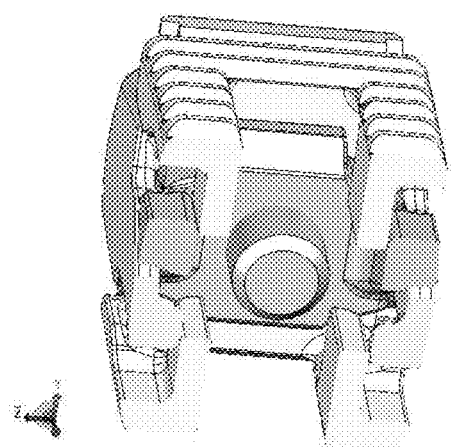
Figure 10D:
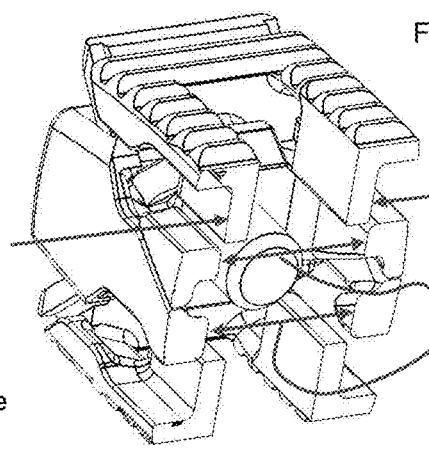
Figure 10E:
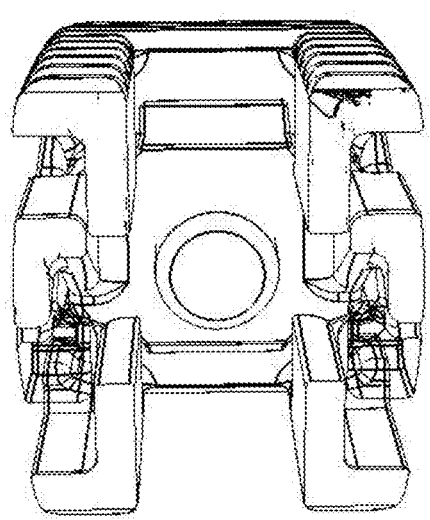

FIG. 10A shows, in section, the components of the assembly in the fully vertically contracted configuration. FIG. 10B shows the same components in a partially vertically expanded configuration. FIG. 10C shows the same components in a fully vertically expanded configuration. FIG. 10D is similar to FIG. 10C but with a slightly different vantage point and labeled to show certain dimensions. FIG. 10E is similar but from yet another vantage point especially to make the urging structure visible.

Figure 11:
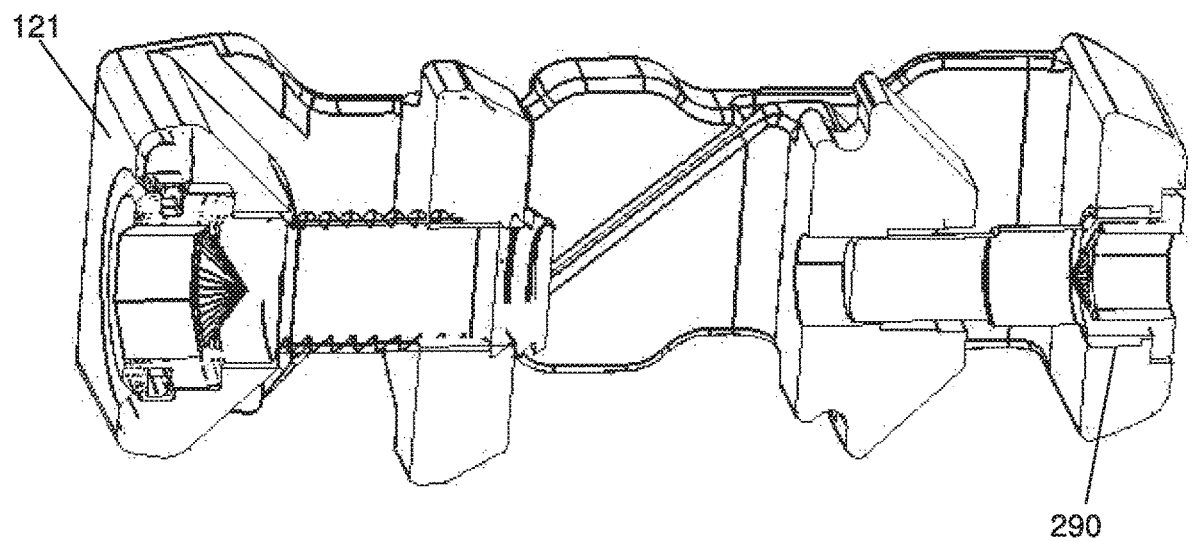

FIG. 11 is a three-dimensional view of a section of the assembled device particularly illustrating the interaction of the urging structure with other components.

Figure 12:
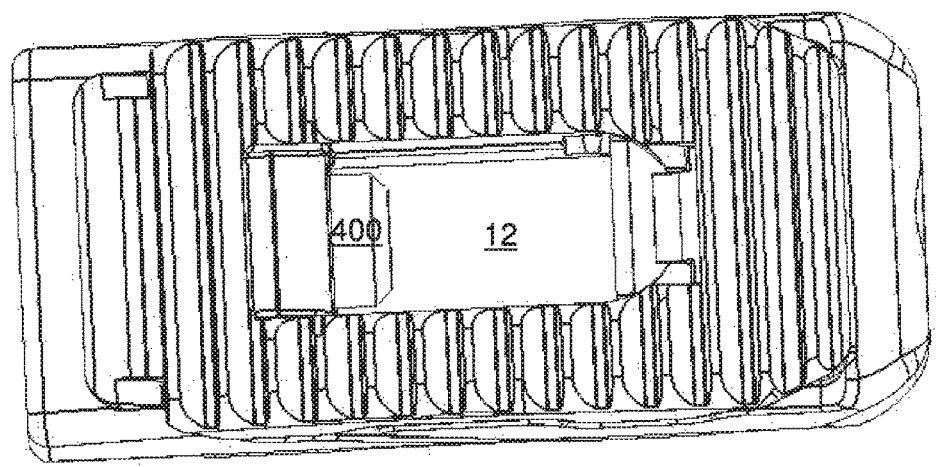

FIG. 12 is a generally top view showing the drivescrew in relation to the central opening through the endplate and the overall device.

Figure 13A:
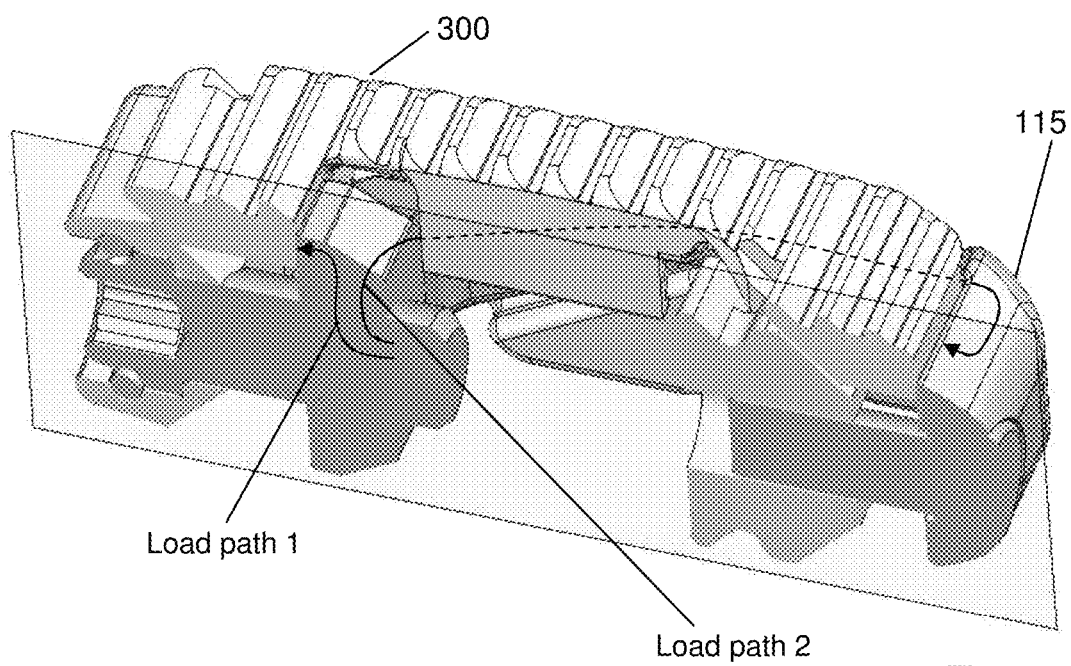
Figure 13B:
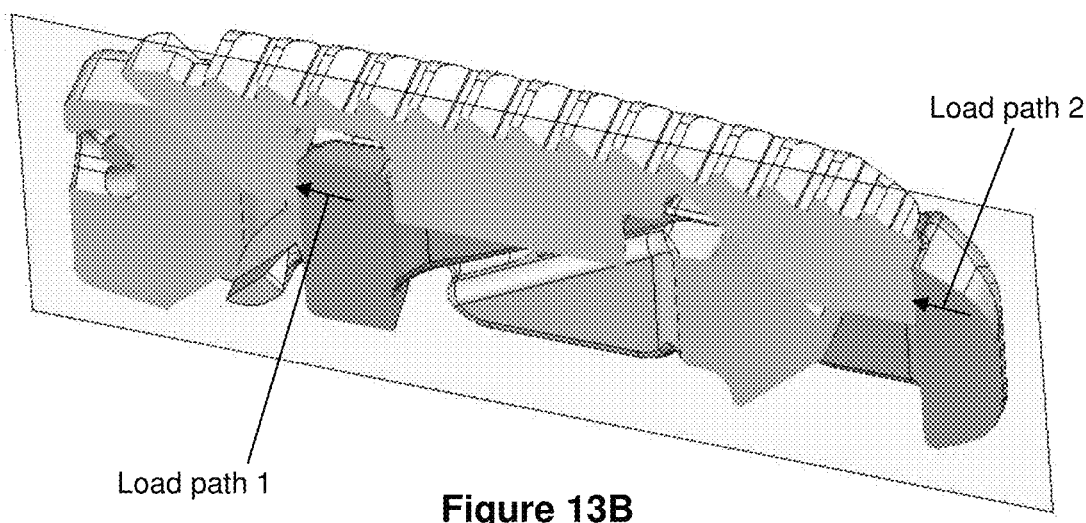
Figure 13C:
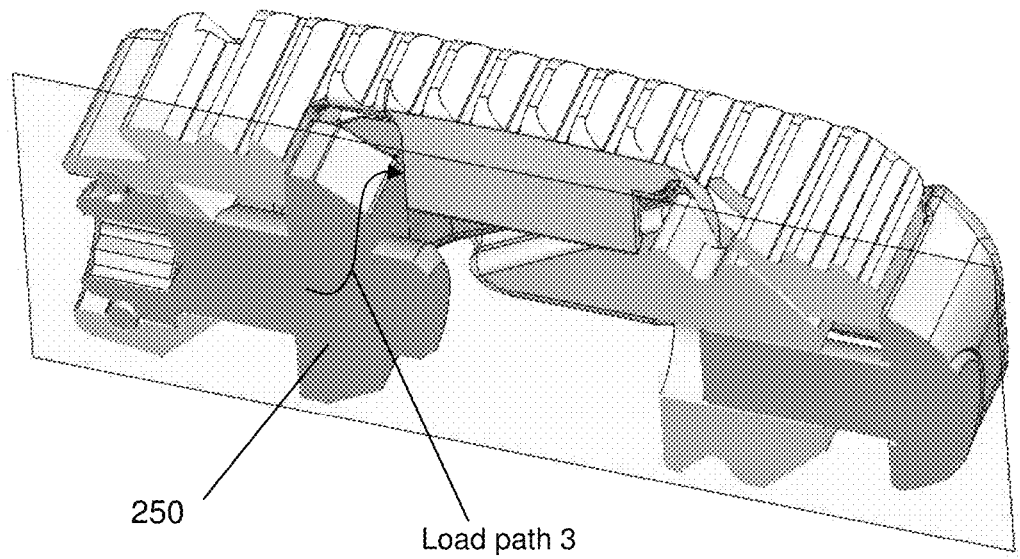
Figure 13D:
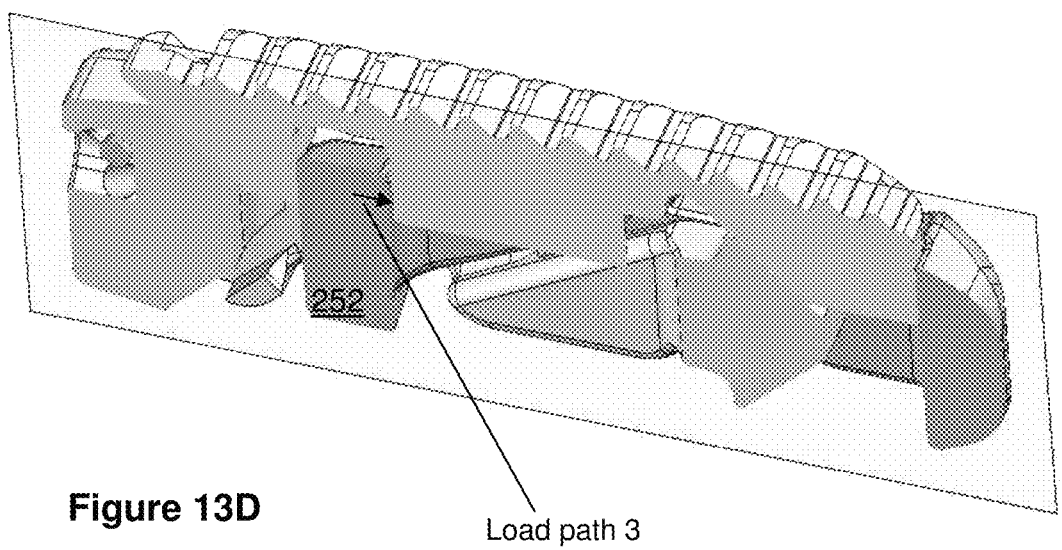

FIG. 13A and FIG. 13B show a load path situation for expansion of the device, with FIG. 13A being a section taken at the centerplane, and FIG. 13B being a section taken at a plane removed from the centerplane. FIG. 13C and FIG. 13D show a load path situation for contraction of the device, with FIG. 13C being a section taken at the centerplane, and FIG. 13D being a section taken at a plane removed from the centerplane.

FIG. 14A shows in cross-section a portion of the device having the drivescrew comprising a polymeric friction element and also a snap-ring. FIG. 14B is a three-dimensional view of the drivescrew in isolation, without the polymeric friction element. FIG. 14C is a three-dimensional view of the drivescrew in isolation, together with its friction element, and with the snap-ring shown exploded away from the drivescrew. FIG. 14D shows the guide pin.

Figure 15A:
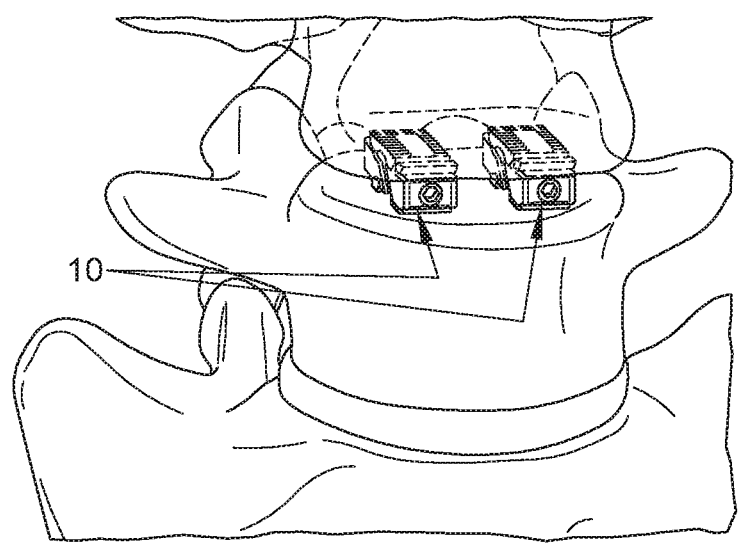
Figure 15B:
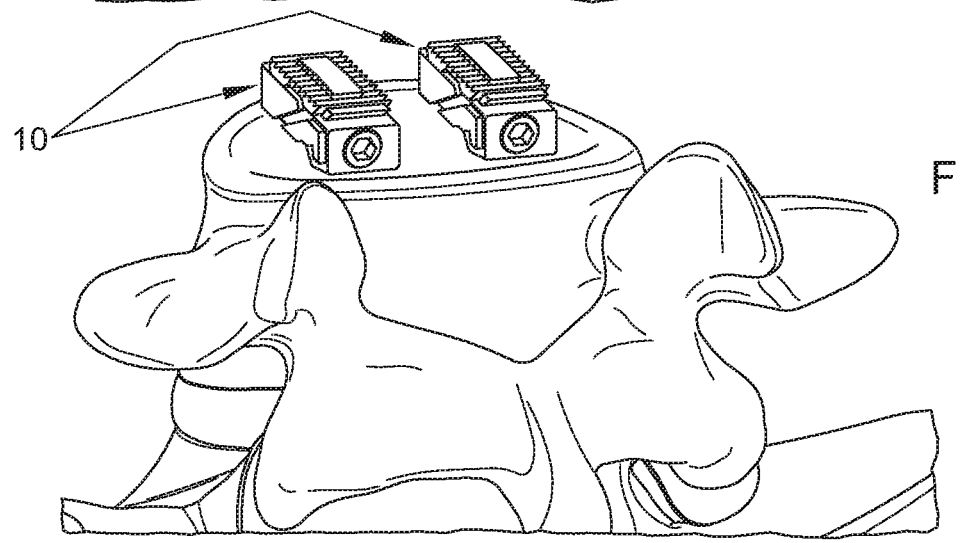
Figure 15C:
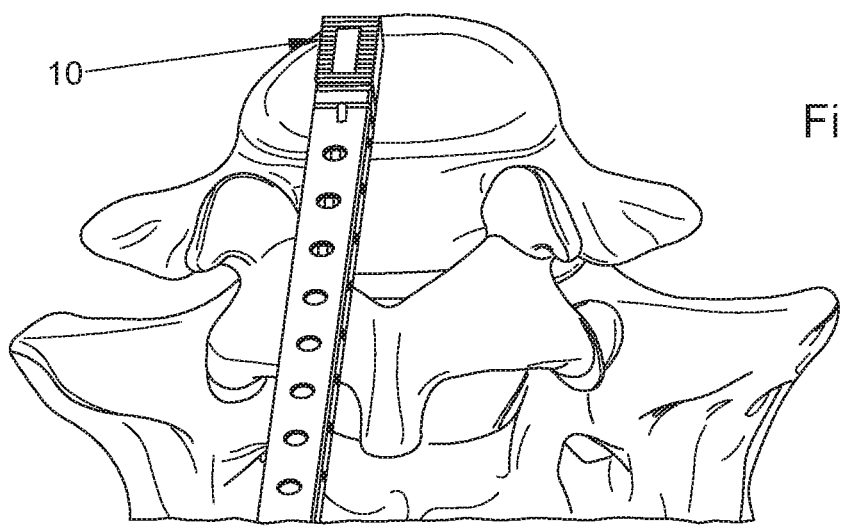

FIG. 15A is a three-dimensional view of two devices placed in an intervertebral disc space, viewed from an anterior vantage point. FIG. 15B is a three-dimensional view of two devices placed in an intervertebral disc space, viewed from a posterior vantage point. FIG. 15C is a three-dimensional view of one of the devices being placed in an intervertebral disc space, also showing a portion of an installation instrument.

DETAILED DESCRIPTION

The present disclosure is directed generally to aspects of a device that can be surgically implanted into a patient, and, more specifically, one or more aspects of a device that can change at least one of its dimensions after being introduced inside the patient's body. For example, some aspects of the present disclosure are directed to entire systems and methods that can be introduced into the intervertebral disc space for purposes of fusing adjacent vertebrae. Some aspects of the present disclosure are directed to one or more aspects of a system and surgical method.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Figure 1A:
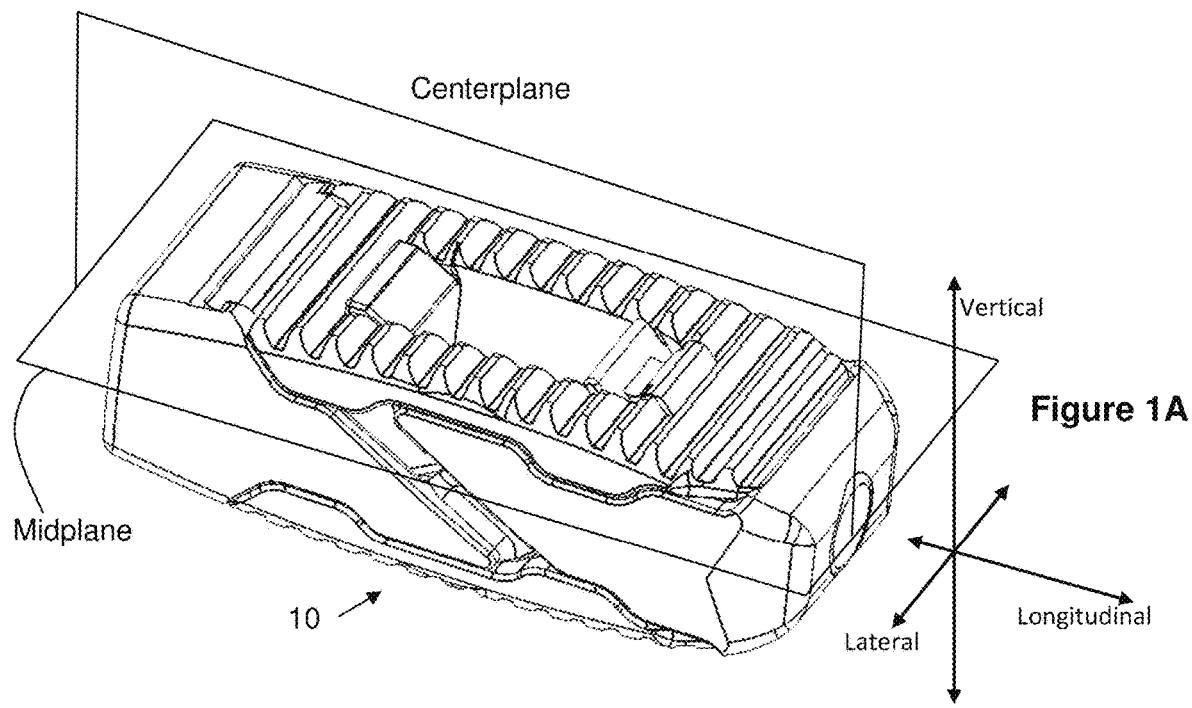
FIG. 1A is a three-dimensional view of an embodiment of the invention, in a vertically contracted configuration.
Figure 1B:
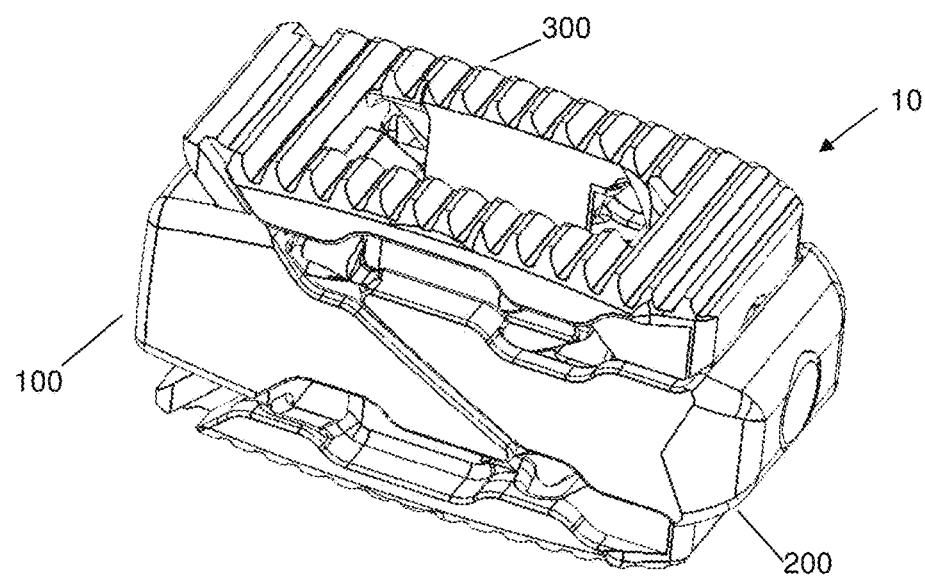
FIG. 1B is a three-dimensional view of an embodiment of the invention, in a vertically expanded configuration.

In an embodiment of the invention, an expandable support device is disclosed that can be inserted into a target surgical site with the device being in a reduced-height configuration. The device is also capable of being reconfigured into an expanded-height configuration. An embodiment is illustrated in FIG. 1A in its reduced-height configuration, and FIG. 1B in its expanded-height configuration. Reference directional designations, namely longitudinal, vertical and lateral, for discussions purposes, are illustrated in FIG. 1A.

Figure 2:
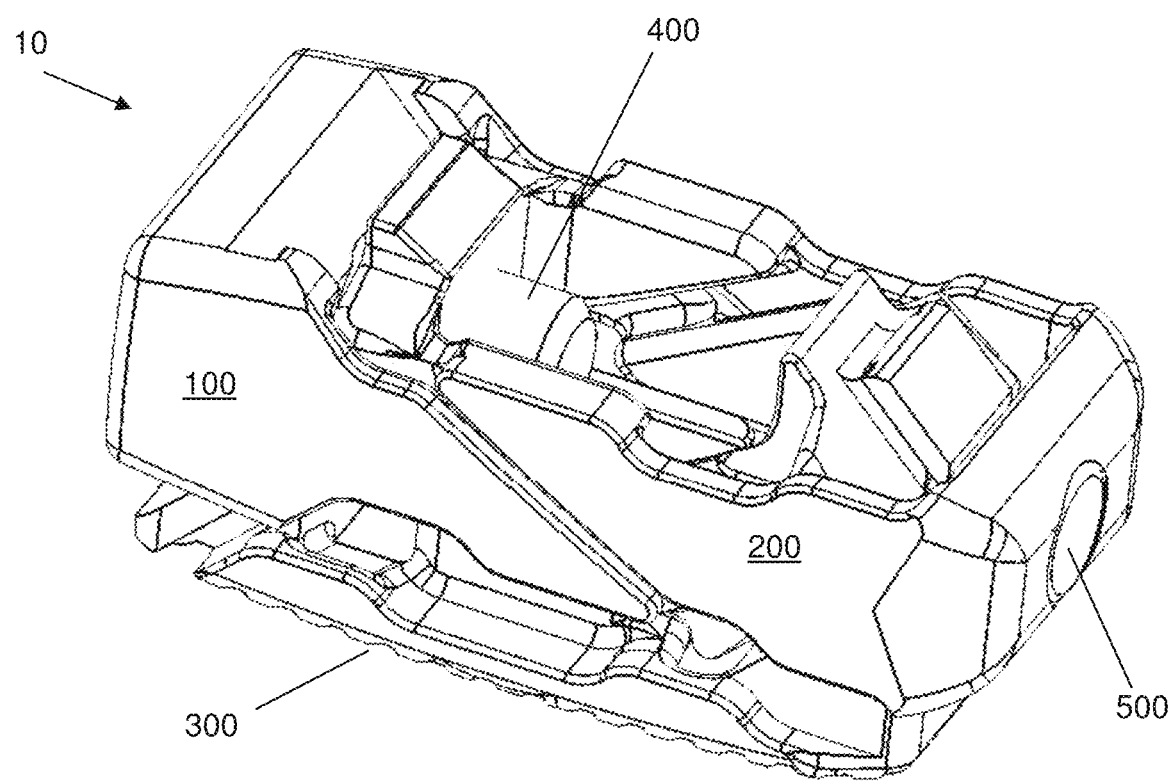
FIG. 2 is similar to FIG. 1B but with one endplate omitted for clarity of illustration.

Referring again to FIGS. 1A-1B and also now to FIG. 2, a device 10 of an embodiment of the invention may comprise a central mechanism located between two endplates and capable of causing the two endplates to move toward or away from each other. (For clarity of illustration, in FIG. 2 one of the endplates is omitted.) The central mechanism may comprise two ring structures, of which one may be designated a proximal ring structure 100 and the other of which may be designated a distal ring structure 200. It can be understood that the designations proximal and distal for the ring structures 100, 200 only refer to a vantage point for descriptive purposes and are not essential characteristics. The proximal ring structure 100 and distal ring structure 200 may be capable of translating relative to each other along an axis that may be referred to as a longitudinal axis. The device 10 may further comprise an actuation mechanism 400 that causes the relative translation between the two ring structures 100, 200 along the longitudinal axis. There may also be a guide mechanism 500 that engages the two ring structures 100, 200 in such a way as to constrain certain degrees of freedom of their relative motion.

Proximal Ring Structure

Referring now to FIGS. 3A-3E, proximal ring structure 100 may first of all comprise a perimeter that extends around a closed path to define an empty interior space that may be referred to as proximal ring structure opening 110. As illustrated, the closed path may comprise, generally speaking, in sequence, first side 121, second side 122, third side 123 and fourth side 124. As illustrated, at least some of these various sides may comprise some segments or surfaces that may be substantially straight lines or planes. Certain features or surfaces of the first side 121 may be parallel to certain features or surfaces of the third side 123, although this is not essential. Certain features or surfaces of the second side 122 may be parallel to certain features or surfaces of the fourth side 124, although this is not essential. The closed path may further comprise rounded corners on the interior, the exterior or both.

As dimensioned in FIGS. 3A-3E, the proximal ring structure 100 may have an external long end-to-end dimension PEL. This dimension may be measured, along the longitudinal direction, between extreme end surfaces, which may be parallel to each other. As dimensioned in FIGS. 3A-3E, the proximal ring structure 100 may have an internal long end-to-end dimension PIL. This dimension may be measured, along the longitudinal direction, between extreme internal surfaces, which may be parallel to each other.

It is further possible to define, for proximal ring structure 100, a "hybrid" dimension PHL as illustrated in FIG. 3C. This dimension is a distance, along the longitudinal direction, between one internal surface and one external surface.

With regard to the sides 122 and 124, it is possible that second side 122 and fourth side 124 may each comprise an offset as illustrated, so that towards one end second side 122 and fourth side 124 are farther away from each other and towards the opposite end, second side 122 and fourth side 124 are closer to each other.

As a consequence of the offset, in the lateral direction, the proximal ring structure 100 may have two different lateral overall external dimensions, the first lateral overall external dimension PEW1 in a first region, and the second lateral overall external dimension PEW2 in a second region. Such lateral dimensions may be measured between surfaces that are parallel to each other. One of the lateral overall external dimensions may be larger than the other lateral overall external dimension, for example, PEW1>PEW2. Similarly, the proximal ring structure 100 may have two different lateral overall internal dimensions, the first lateral overall internal dimension PIW1 in a first region, and the second lateral overall internal dimension PIW2 in a second region. Such lateral dimensions may be measured between surfaces that are parallel to each other. One of the lateral overall internal dimensions may be larger than the other lateral overall internal dimension, for example, PIW1>PIW2.

Furthermore, it is possible that PIW1>PEW2. The implantable device 10 may have a central mechanism comprising a proximal ring structure 100 and a distal ring structure 200 (described elsewhere herein), in which one of the ring structures has four sides, and of those four sides, two opposed sides (122, 222) have offsets such that there can be defined a first inside width PIW1 and a second inside width PIW2 and a first outside width PEW1 and a second outside width PEW2, wherein the smaller of the outside widths PEW2 is less than the larger of the inside widths PIW1. This relation may be true for either the proximal ring structure 100 or the distal ring structure 200 or both.

Referring now to FIG. 4, a prism is defined here to be a three-dimensional shape that is defined by a two-dimensional base shape that is repeated or extruded identically in a third direction perpendicular to the base shape. That direction may be referred to as the prismatic axis direction. The proximal ring structure opening 110 may be surrounded by an internal perimeter surface such that at least a substantial portion of the internal perimeter surface would coincide with an appropriately shaped prism having a prismatic axis direction. As illustrated, the proximal ring structure 100 has a proximal ring structure opening 110 much of whose perimeter would coincide with a prism whose two-dimensional base shape is a shape that may be described generally as a narrower rectangular region merging with a wider rectangular region with all or some corners rounded using segments of curves such as circular arcs. The implantable device 10 may have a central mechanism comprising a proximal ring structure 100 and a distal ring structure 200 (described elsewhere herein), in which at least one of the ring structures 100, 200 has a central opening 110, 210 that has a first internal width dimension PIW1 and a second internal width dimension PIW2, wherein the first internal width dimension PIW1 is different from the second internal width dimension PIW2. This relation may exist for either the proximal ring structure 100 or the distal ring structure 200. As illustrated in FIG. 4, that described base shape may be extruded or repeated in the dimension perpendicular to the plane of the described shape to produce a prismatic shape, such that a significant portion of the internal surface of the proximal ring structure opening 110 (or that portion of the internal surface of the proximal ring structure opening 110 that is itself a prismatic surface) may coincide with the external surface of the prism. (In FIG. 4, some of the repetitions of the base shape of the extrusion are omitted for clarity.) Of course, it would be possible to design the proximal ring structure 100 so that its proximal ring structure opening 110 is defined by a prismatic base shape other than the described merged-rounded-rectangular shape. It is understood that, depending on details of design of the proximal ring structure 100, it is possible to have local irregularities in the internal perimeter surface of the proximal ring structure opening 110, so that the internal surface of the proximal ring structure opening 110 might not coincide everywhere with the described prism. Nevertheless, even if with only a substantial portion of the internal surface of the proximal ring structure opening 110 coincides with the described prism, the described prism may serve to define, by its prismatic axis direction, a direction of the proximal ring structure opening 110. More generally, a direction of the proximal ring structure opening 110 may be defined as the direction of the axis of a prismatic structure when the prismatic structure is in the orientation that best allows a prism of cross-sectional shape similar to that of the proximal ring structure opening 110 to fill or pass through the proximal ring structure opening 110. This axis may generally coincide with the vertical direction of device 10.

With continued reference to FIGS. 3A-3E and additionally referring to FIGS. 5A-5C, the proximal ring structure 100 may have a first ramp 131 and a second ramp 132. First ramp 131 and second ramp 132 may be located in the same direction from the midplane of device 10 at opposite ends of proximal ring structure opening 110. For example, the proximal ring structure 100 may have a midpoint in the longitudinal, i.e., proximal-distal, direction. First ramp 131 may be proximal of the midpoint and second ramp 132 may be distal of the midpoint. For example, first ramp 131 may be part of first side 121, and second ramp 132 may be part of third side 123. First ramp 131 and second ramp 132 may slope in substantially the same orientation, i.e., if from a particular viewing direction first ramp 131 slopes from lower left to upper right, second ramp 132 may also slope from lower left to upper right. The proximal ring structure 100 may have a first ramp angle 141 is defined as illustrated in FIG. 5A. The proximal ring structure 100 may have a second ramp angle 142 defined as illustrated in FIG. 5A. Those two ramp angles 141, 142 may be equal to each other, i.e., ramps 131 and 132 may be parallel to each other.

Proximal ring structure 100 may also comprise additional opposed ramps as shown in FIG. 5B. If first ramp 131 and second ramp 132 are considered to be on the top of the proximal ring structure 100, then ramp 181 and ramp 182 may be considered to be on the bottom of proximal ring structure 100. Ramp 181 may be identical to or a mirror image of first ramp 131. Ramp 182 may be identical to or a mirror image of second ramp 132. The midplane may be a plane of symmetry between features on the top of proximal ring structure 100 and features on the bottom of proximal ring structure 100.

If ramps 131 and 132 involve a T-shaped projection or a T-shaped groove as illustrated, there may be additional ramp surfaces associated with the basic ramps 131, 132. Such surfaces may be parallel to basic ramp surfaces 131, 132. (There may be still other surfaces of proximal ring structure 100 that are perpendicular to those ramp surfaces.) For example, ramp surface 131a may be parallel to ramp surface 131, and may face toward ramp surface 131. A possible ramp surface 164a is discussed elsewhere herein. Associated with ramp surface 132 there may be ramp surface 132a facing toward ramp surface 132, and there may also be ramp surface 132b, which may face in the same orientation as ramp surface 132.

First ramp 131 may have an engagement feature such that a complementary structure that it interacts with may engage with first ramp 131 in a way that guides motion, or prevents disassembly in at least some situations, or both.

Second ramp 132 may have an engagement feature also, which could be geometrically similar to or geometrically different from the engagement feature present with first ramp 131.

In general an engagement feature could comprise a protrusion and a receiver, one of them on a ramp and the other on a complementary surface or component. First of all, it is possible that a protrusion and a receiver could constrain so as to keep the device assembled or prevent disassembly under at least some circumstances or with respect to as certain direction of possible disassembly motion. Such engagement that prevents disassembly by motion in a direction generally perpendicular to the ramp surface may be referred to as interlocking. Alternatively, it is possible that a protrusion and receiver could merely cooperate to form a guide to constrain certain degrees of freedom of motion, without preventing the described disassembly in the described direction of motion. This may be referred to as non-interlocking.

One of the ramps 131, 132 may have an engagement feature that is a protrusion and the other of the ramps 131, 132 may have an engagement feature that is a receiver. As illustrated, second ramp 132 has a protrusion feature and first ramp 131 has a receiving feature. However, other designs are also possible. Various surfaces of these engaging geometries may be parallel to each other or perpendicular to each other; as illustrated the various protruding or receiving features have cross-sectional shapes that are rectangles or portions of rectangles. The implantable device 10 may have a central mechanism comprising a proximal ring structure 100 and a distal ring structure 200 (described elsewhere herein), in which the proximal ring structure 100 has a first ramp 131 and a second ramp 132, in which the first ramp 131 comprises a receiving structure capable of engaging a first complementary shape, and the second ramp 132 comprises a protruding shape capable of engaging a second complementary shape.

As illustrated, the two ramps 131, 132 have engagement geometries that are in the same shape family as each other, i.e., both involve a T-shaped projection engaging a T-shaped receiver that is complementary to it. However, it is also possible that the two ramps 131, 132 could have engagement features that are not the same shape family as each other (e.g., one could involve T-shape and the other could involve dovetail), or one ramp could involve a feature that prevents disengagement by motion generally perpendicular to the ramp surface and another ramp might only involve a feature that guides motion without preventing disassembly as does not prevent disassembly as described, and might not involve any such interlocking feature.

It can be noted that it is possible to have protrusion and receiving features that prevent disengagement between engaging components that involves motion in the direction of simply pulling the ramps apart from each other in a direction generally perpendicular to the ramp surfaces. The described T-shaped projection and T-shaped groove accomplish such prevention of disengagement. The prevention of disengagement could alternatively be accomplished by a dovetail engagement such as a trapezoidal shape engaging with a complementary shape, or by still other geometry. Alternatively it is possible to have protrusion and receiving features that restrict or guide some degrees of freedom of motion while not actually preventing the described disengagement in the described direction of motion. An example of such a geometry would be a projection whose cross-section is a simple rectangle, and a receiving feature that is complementary to it. Of course, still further, it would also be possible to have a mixture of such kinds of features in various ramps within the same device or component.

As illustrated, the engagement features of the first ramp 131 and the second ramp 132 in proximal ring structure 100 are of the same type as each other, i.e., both are in the form of either a T-shaped groove or a T-shaped projection. As illustrated, the one engagement feature is a T-shaped projection and another engagement feature is a T-shaped receiver, each of which is suitable to mate with a complementary shape. However, the various ramp engagement features could also be different from each other.

In FIGS. 6A-6C are shown various specific dimensions of the engagement features of proximal ring structure 100. Some of the features pertain to the protrusion and some pertain to the receiver. Interrelationships of these dimensions with dimensions of other parts are described elsewhere herein.

It can further be noted that in connection with first ramp 131 and second ramp 132, there may be associated still other surfaces that may be parallel to first ramp 131 and second ramp 132. These other surfaces may be associated with engagement features. In describing ramps, the description outward-facing is used herein to describe a ramp surface such as 131, 132 that faces the overall corresponding component against which the ramp faces, and which could potentially bear force against its face during vertical expansion of the overall device 10. The opposite description, of an inward-facing ramp, is for a ramp surface such as 131*a*, 132*a* that serves as a capture feature preventing disassembly of the device by disassembly motion of ramp surfaces away from each other perpendicular to the ramp surface, or which bears or could potentially bear force during vertical contraction of the overall device 10. It can further be noted that sometimes there may be a second parallel outward-facing surface such as 132*b* related to a particular ramp structure. Depending on dimensions and tolerances in proximal ring structure 100 and also in an engaging part, either or both of such surfaces 131, and 132, 132*b* could be active in sliding and generation of forces involving that ramp for causing vertical expansion of the device 10.

The proximal ring structure 100 may, on its second side 122 and fourth side 124 (the portions of those sides that are larger in the lateral direction) have side ramps 162, 164 that may be a portion of a generally trapezoidal shape. These side ramps 162, 164, although rounded surfaces may be present, may have some straight-line or planar segments that have a defined slope. Side ramp 162 may be part of second side 122, and side ramp 164 may be part of fourth side 134. The side ramps or cutouts 162, 164 may have a slope corresponding to the angled sides of the generally trapezoidal shape. This slope of side ramps or cutouts 162, 164 may be identical to the slope of ramp 131, or ramp 132, or both. This is discussed further elsewhere herein. These side ramps 162, 164 are illustrated as being simple ramps that do not comprise engagement features for engagement with a complementary feature of another component. Geometric transitions to or from side ramps 162, 164 may comprise rounded corners. It is also possible that a ramp such as 164 may have a flat surface that continues in an irregular shape as designated 164*a* in FIG. 5C.

It is possible to define a centerplane that extends in a vertical direction and includes the longitudinal axis of the device 10. It can further be noted that the first ramp 131 and the second ramp 132 are ramps that straddle both sides, in a lateral direction, of a centerplane. In contrast, side ramp 162, exists entirely on one side (in a lateral direction) of the centerplane, and side ramp 164 exists entirely on the other side (in the lateral direction) of the centerplane. It can further be noted that side ramps 162, 164 may be coplanar with each other and that ramp 131 may be parallel to but not coplanar with side ramps 162, 164. Side ramps 162, 164 may also be referred to as overhang-receiving cutouts, due to their receipt of and interaction with overhangs of an endplate described elsewhere herein. The device 10 may have a central mechanism comprising a proximal ring structure 100 and a distal ring structure 200 (described elsewhere herein), such that the proximal ring structure 100 has a first ramp such as 131 or 132 that extends continuously across the centerplane, and such that the proximal ring structure 100 also has two additional ramps such as 162, 164, one on each side of the centerplane, and not intersecting the centerplane, with the two additional ramps 162, 164 being coplanar with each other.

It can be noted that the proximal ring structure 100, as described and illustrated, comprises both at least one ramp that has an engagement feature, such as ramps 131, 132 (possibly 131a, 132a depending on dimensions and tolerances), and at least one ramp that does not have an engagement feature, such as 162, 164. An engagement feature can refer to either a protrusion or a receiving feature, any of which may be either non-interlocking or interlocking. It is possible that a ramp having an engagement feature and a ramp not having an engagement feature may occur on a particular direction relative to the proximal-distal midpoint of proximal ring structure 100, with respect to the longitudinal direction of the device 10. The implantable device 10 may have a central mechanism comprising a proximal ring structure 100 and a distal ring structure 200 (described elsewhere herein), in which the proximal ring structure 100 has a plurality of ramps such as 131, 132, 162, 164, in which at least one of the ramps has an engagement feature and another of the ramps does not have an engagement feature. An engagement feature may be either a protrusion or a receiving feature, and may be either interlocking or non-interlocking. It can further be noted that the proximal ring structure 100, as described and illustrated, contains three different outward-facing ramp surfaces, such as 131, 132 and either 162 or 164 that are parallel to each other but are located in different respective non-coplanar planes. More generally, 131, 132, 132b and the grouping of 162, 164 may all be outward-facing ramp surfaces that are parallel to each other but are located in different respective non-coplanar planes. Ramp surfaces 131a, 132a may also be parallel to those others as well although not themselves being outward-facing.

It can further be noted that on any given direction from the proximal-distal midpoint of the proximal ring structure 100, there can be a mixture of different kinds of ramps: one or more ramps that have no type of engagement feature, along with one or more ramps that have some type of engagement feature. The ramps used in this description can be specified as outward-facing as in the illustrations or could be any type of ramp either outward-facing or not.

It can further be noted that a T-shaped projection in combination with a complementary-shaped receiver such as a T-shaped slot, as illustrated, constrains against disassembly in a direction perpendicular to the ramp surface, and may be referred to as interlocking. A dovetail (trapezoidal cross-section) in combination with a complementary-shaped receiver would also constrain against disassembly. Other shapes of engagement features are possible. For example, a protrusion of simple rectangular cross-section, in combination with a complementary-shaped receiving structure, would constrain certain degrees of freedom of motion but would not actually constrain against disassembly in a direction perpendicular to the ramp surface, and may be referred to as non-interlocking.

It is possible to define the proximal-distal midpoint that is midway between the extremes of the proximal ring structure 100 in a proximal-distal (longitudinal) direction. It can be noted that within the proximal ring structure 100, there can be as many as four different outward-facing ramp surfaces that are parallel with each other but all lie in different planes. These can be 132, 132b, 131 and the grouping of 162, 164. Further counting ramp surfaces that are not outward-facing, there may additionally be ramp surfaces 131a, 132a, which also may be parallel to the just-mentioned ramp surfaces and need not be coplanar with any of them. In one direction from proximal-distal midpoint of proximal ring structure 100, counting ramp surfaces that may be either outward-facing or non-outward-facing, there may be the following parallel non-coplanar ramp surfaces: 131, 131a and the grouping 162, 164. In the other direction from the proximal-distal midpoint, there may still further be ramp surfaces 132, 132a, 132b, being parallel to and non-coplanar with each other.

A ramp surface can have a slope direction, which may be defined such that the slope direction is contained in the ramp surface plane, and such that the slope direction and the longitudinal direction of the implantable device 10 can form an angle. With respect to the slope direction, a width can be defined as being measured within the ramp plane in a direction perpendicular to the slope direction, and measuring the extent within which the ramp surface is truly planar, i.e., to a point at which the surface departs from planarity such as by a corner or a fillet etc. In the example as shown, it can be observed that the width of surface of ramp 131 or 132 or 132a is different from the width of surface of ramp 162 on second side 122 or ramp 164 on the fourth side 124. Similarly, other comparisons of ramp surfaces on the proximal ring structure 100 would also show unequal ramp widths. It is further possible, alternatively, that either or both of the surface of second side 122 in the region illustrated by ramp 162, and the surface of fourth side 124 in the region illustrated by ramp 164, may, instead of a planar ramp surface, have a rounded surface (not shown) extending from the interior to the exterior of that respective side. Such a rounded surface may have a tangent line that is straight generally lying in a vertical plane and may be suitable for a corresponding ramp surface, such as a ramp surface of an endplate, to slide along it. Such a rounded surface may function similarly to a ramp surface (such as 162, 164) in interacting with a corresponding ramp surface of another component of device 10.

The proximal ring structure 100 may have, at one end such as first end 121, an interface with the actuation mechanism 400. The interface with the actuation mechanism 400 may comprise a cylindrical hole 180 in first end 121 of proximal ring structure 100, or other similar details as known in the art. The cylindrical hole may comprise a counterbore with an internal groove 196 as described elsewhere herein, or other features. The proximal ring structure 100 may have a feature (not shown) suitable to interact with a surgical instrument such as to be grasped by a surgical instrument. The surgical instrument interface feature may be at the same end of the proximal ring structure 100 as the actuation mechanism 400.

At an opposed end, such as at third side 123, proximal ring structure 100 may have an interface with a guide mechanism 500. The interface with the guide mechanism 500 may comprise a hole 190 as illustrated, or alternatively a cylindrical post, or means to join with any such feature, or other details known in the art. Hole 190 may be internally threaded, or may be a simple cylindrical hole, or other design as known in the art.

Distal Ring Structure

Referring now to FIGS. 7A-7C, there may also be provided a distal ring structure 200. Some features of distal ring structure 200, such as its general shape, may have similarity to corresponding features of proximal ring structure 100, but other features may be different. Distal ring structure 200 may comprise a perimeter that extends around a closed path to define an empty interior space that may be referred to as distal ring structure opening 210. As illustrated, the closed path may comprise, generally speaking, in sequence, first side 221, second side 222, third side 223 and fourth side 224. As illustrated, at least some of these various sides may comprise some segments or surfaces that may be substantially straight lines. Certain features or surfaces of the first side 221 may be parallel to certain features or surfaces of the third side 223, although this is not essential. Certain features or surfaces of the second side 222 may be parallel to certain features or surfaces of the fourth side 224, although this is not essential. The closed path may further comprise rounded corners either internally or externally.

The distal ring structure 200 may have a blunt nose 215 suitable to displace bodily tissue without injuring it as the device 10 is advanced into bodily tissue during surgery.

As dimensioned in FIG. 7B, the distal ring structure 200 may have an external long end-to-end dimension DEL. This dimension may be measured, along the longitudinal direction, between extreme end surfaces, which may be parallel to each other. Also as dimensioned in FIG. 7, the distal ring structure 200 may have an internal long end-to-end dimension DIL. This dimension may be measured, along the longitudinal direction, between extreme internal surfaces, which may be parallel to each other.

It is further possible to define, for distal ring structure 200, a "hybrid" dimension DHL as illustrated in FIG. 7B. This dimension is a distance, along the longitudinal direction, between one internal surface and one external surface.

It is further possible that second side 222 and fourth side 224 may each comprise an offset as illustrated, so that towards one end second side 222 and fourth side 224 are farther away from each other and towards the opposite end, second side 222 and fourth side 224 are closer to each other.

As a consequence of the offset, in the lateral direction, the distal ring structure 200 may have two different lateral overall external dimensions, the first lateral overall external dimension DEW1 in a first region, and the second lateral overall external dimension DEW2 in a second region. Such lateral dimensions may also be measured between surfaces that are parallel to each other. One of the lateral overall external dimensions may be larger than the other lateral overall external dimension, for example, DEW1>DEW2. Similarly, the distal ring structure 200 may have two different lateral overall internal dimensions, the first lateral overall internal dimension DIW1 in a first region, and the second lateral overall internal dimension DIW2 in a second region. Such lateral dimensions may also be measured between surfaces that are parallel to each other. One of the lateral overall internal dimensions may be larger than the other lateral overall internal dimension, for example, DIW1>DIW2. Furthermore, it is possible that DIW1>DEW2.

The distal ring structure 200 may have, at one end, an interface with the actuation mechanism 400, and may have, at an opposed end, an interface with the guide mechanism 500. The interface with the actuation mechanism 400 may comprise a threaded hole 270 in first side 221, suitable to receive a threaded member.

The distal ring structure opening 210 may have a distal ring structure opening direction, which may be defined in a manner similar to that discussed for the proximal ring structure opening 110.

It is further possible that the distal ring structure 200 may comprise a projection in the vertical direction, which may be referred to as an urging structure 250. As illustrated, the urging structure 250 projects both upwardly and downwardly in the vertical direction from first side 221. This urging structure 250 may interface with other components of the device 10 as described elsewhere herein. The urging structure 250 may have a dimension in the longitudinal direction DULON as defined in FIG. 7A, which dimension may be involved in interfacing with other components as discussed elsewhere herein. Also, the most vertically-extending portion of urging structure 250 may have a lateral dimension DULAT that is less than the smaller internal width DIW2 of distal ring structure 200 adjacent to urging structure 250. Also, where the urging structure 250 merges with the rest of end at first side 221, there may be a transition shape 252 that also may be involved in interfacing with other components as discussed elsewhere herein.

The distal ring structure 200, on its second side 222 and fourth side 224 (the portions of those sides that are larger in the lateral direction) may have overhang-receiving cutouts or ramps 262, 264 that may be a portion of a generally trapezoidal shape. The cutouts or ramps 262, 264 may have a slope corresponding to the angled sides of the trapezoidal shape. This slope may be equal to the slope of any or all of ramps 131, 131a, 132, 132a, 132b of proximal ring structure 100. Shape transitions associated with the trapezoidal shape may comprise rounded corners. This is discussed further elsewhere herein.

In the longitudinal direction, the urging structure 250 may be such as to fit between the stability bar 370 and the depending structure from the endplate 300 that forms the edge of endplate central opening 310. For example, in the longitudinal direction, the urging structure 250 may have two opposed sides that are generally parallel to each other and define an external dimension between them. Similarly, the stability bar 370 and the depending structure from the endplate 300 that forms the edge of endplate central opening 310 may have surfaces that face each other and are generally parallel to each other and define an internal dimension between them in the longitudinal direction. The dimension of urging structure 250, in the longitudinal direction, may be just slightly less than or may be approximately equal to, the distance between the internal surface of endplate central opening 310 and the facing edge of stability bar 370.

Interrelationships Between the Two Ring Structures

Generally speaking, the proximal ring structure 100 and the distal ring structure 200 may have with each other an intertwining relationship so that in either the lateral or the longitudinal direction, in some places one ring structure is more exterior and in other places the other ring structure is more exterior. When considering the proximal ring structure 100 and the distal ring structure 200 in conjunction with each other, it is possible to note some dimensional interrelationships that may exist between the two ring structures.

When the proximal ring structure 100 and the distal ring structure 200 are assembled together in a sub-assembly, the proximal ring structure opening 110 may partially but not completely overlap with the distal ring structure opening 210 when viewed along the first opening direction. The assembly containing proximal ring structure 100 and distal ring structure 200 can have an open region 12 passing through the center of the device 10 along the direction of the proximal ring structure opening 110 and the distal ring structure opening 210. The dimensions of this open region 12 may vary with the relative positions of proximal ring structure 100 and distal ring structure 200 within their range of permitted motion, but the open region 12 may exist to at least some extent throughout the permitted range of relative motion of proximal ring structure 100 and the distal ring structure 200. The sub-assembly may allow relative translational motion between the two ring structures 100, 200 and may leave some open central region 12 for all permitted translational positions of the two ring structures 100, 200.

It is possible that the larger external width dimension PEW1 of the proximal ring structure 100 may be at least approximately equal to the larger external width dimension DEW1 of the distal ring structure 200. This may provide a somewhat consistent external size envelope of the overall device 10. It is possible that the smaller internal width dimension PIW2 of the proximal ring structure 100 may be at least approximately equal to the smaller internal width dimension DIW2 of the distal ring structure 200. This may help to provide a somewhat consistent size of open region 12 that generally passes in the vertical direction through the sub-assembly of proximal ring structure 100 and distal ring structure 200. It is further possible that PEW2 may be at least approximately equal to DEW2 and that PIW1 may be at least approximately equal to DIW1.

In order to permit the intertwining or nesting of the two ring structures 100, 200, the appropriate internal width of one ring structure may be at least a slight amount greater than the corresponding external width of the other ring structure. For example, the larger internal width, PIW1, of proximal ring structure 100, may be larger than the smaller external width DEW2 of distal ring structure 200. Similarly, the larger internal width, DIW1, of distal ring structure 200 may be larger than the smaller external width PEW2 of proximal ring structure 100. The existence of a slight clearance gap between those respective dimensions may be chosen so as to allow relative motion, especially translation, to occur freely between those two ring structure components. However, the clearance gap may be small enough so that it limits any permitted angular tilting of one ring structure with respect to the other ring structure, around an axis coincident with the longitudinal direction, to a suitably small magnitude.

In an embodiment of the invention, the proximal ring structure 100 and the distal ring structure 200 may be arranged such that, in all permitted positions of the distal ring structure 200 relative to the proximal ring structure 100, in a section of the device 10 taken along a longitudinal direction, there is a first end at first side 121 of the proximal ring structure 100, followed by a first end at first side 221 of the distal ring structure 200, followed by a second end at third side 123 of the proximal ring structure 100, followed by a second end at third side 223 of the distal ring structure 200.

In an embodiment of the invention, there may be provided an implantable device having a central mechanism comprising a proximal ring structure and a distal ring structure, wherein, in some cross-section taken in a first plane perpendicular to a longitudinal direction, there is in sequence progressing in a lateral direction the proximal ring structure 100 followed by the distal ring structure 200 followed by some empty space followed by the distal ring structure followed by the proximal ring structure, and wherein, in some other cross-section taken in a second plane perpendicular to the longitudinal direction, there is in sequence progressing in a lateral direction the distal ring structure followed by the proximal ring structure followed by some empty space followed by the proximal ring structure followed by the distal ring structure.

In an embodiment of the invention, there may be provided an implantable device having a central mechanism comprising a proximal ring structure 100 and a distal ring structure 200 and having a central opening, wherein, in sequence progressing around the perimeter of the central opening, the central opening is bounded on the first end by the proximal ring structure 100, and then on the first side is bounded first by the proximal ring structure 100 and then by the distal ring structure 200, and then on the second end is bounded by the distal ring structure 200, and then on the second side is bounded first by the distal ring structure 200 and then by the proximal ring structure 100.

With respect to still other directions, it is possible that proximal ring structure 100 and the distal ring structure 200 may have roughly equal heights along the direction of the proximal ring structure opening 110 and the distal ring structure opening 210 i.e., generally the vertical direction of the device 10. It is also possible that proximal ring structure 100 and the distal ring structure 200 may have roughly equal external lengths, i.e., PEL and DEL may be roughly equal. It is also possible that proximal ring structure 100 and the distal ring structure 200 may have roughly equal internal lengths, i.e., PIL and DIL may be roughly equal. It is also possible that proximal ring structure 100 and the distal ring structure 200 may have roughly equal hybrid dimensions, i.e., PHL and DHL may be roughly equal.

Also, the transition along second and fourth sides 122, 124 and 222, 224 of proximal ring structure 100 and distal ring structure 200 respectively, may involve diagonal segments. These diagonal segments may be arranged so that at the expanded-height configuration the diagonal segments either contact each other or have at least a small amount of space between them, and at the reduced-height configuration the diagonal segments have a greater amount of space between them.

When assembled together in an assembly, the proximal ring structure 100 and the distal ring structure 200 may be movable with respect to each other. Such motion may include translation along the longitudinal direction. Such motion may be driven by an actuation mechanism 400 and may further be guided by a guide mechanism 500, both described elsewhere herein. FIGS. 8A-8D shows the proximal ring structure 100 and the distal ring structure 200, with all other components omitted for clarity of illustration, at two different relative positions for different horizontal translation.

Of the proximal ring structure 100 and the distal ring structure 200, there may be considered to be a driving ring structure and a driven-ring structure. The proximal ring structure 100 may be considered to be driving the ring structure in the sense that it may be most proximal to the surgeon and may be interfaced by an insertion tool. The distal ring structure 200 may be considered to be the driven ring structure, which is movable with respect to the driving ring structure. Such movable relation may include at least translation. Actuation mechanism 400 may comprise a drivescrew. As described herein, the driven ring structure may be the ring structure that has an internal thread that receives and threadingly engages the threads of the drivescrew 450. The driving ring structure may be considered to be the ring structure that has unthreaded interaction with the drivescrew. However, it would also be possible to have configurations in which the opposite is true as far as which ring structure has threaded interaction with the drivescrew and which ring structure has unthreaded interaction with the drivescrew.

As a result of some of the dimensional interrelationships such as those involving internal width dimensions, it is possible that when the proximal ring structure 100 and the distal ring structure 200 are assembled to each other, the appearance of the central opening or region 12 that is clear of both the proximal ring structure 100 and the distal ring structure 200 may have the general appearance of a rectangle, possibly with rounded corners. This is illustrated with a view along the vertical direction in FIG. 8B.

It can be described that the central opening or region 12 between the proximal ring structure 100 and the distal ring structure 200 may be bounded, in sequence progressing in a lateral direction, on a first side by the proximal ring structure 100, then on a second side by the proximal ring structure 100 followed by the distal ring structure 200, then on a third side by the distal ring structure 100. More specifically, when viewed along the longitudinal axis, the central opening between proximal ring structure 100 and distal ring structure 200 may be bounded by a perimeter of the central opening such that the central opening is bounded on an end by the first side 121 of proximal ring structure 100, is bounded on its first side by the second side 122 of proximal ring structure 100 and thence by the second side 222 of distal ring structure 200, then is bounded at an end by the third side 223 of distal ring structure 200, then is bounded on another side by the fourth side 224 of distal ring structure 200 and then by the fourth side 124 of proximal ring structure 100.

Endplates

Referring now to FIGS. 9A-9G, an embodiment of the invention may further comprise a top endplate 300, as described here. There may also be a bottom endplate 300. As illustrated, the top endplate 300 and bottom endplate 300 are geometrically identical to each other and are placed on opposite sides of a central plane of symmetry of the device. It is also possible that the top and bottom endplates 300 could be mirror images of each other with respect to some plane of symmetry such as the midplane of the device 10. Of course, it is also possible that geometric differences could exist between the two endplates.

The endplate 300 may have an external surface 302 suitable to be in contact with a vertebra or other bony surface of a patient's body, and may have an underside surface opposed to the external surface 302. The endplate may have an axis, which may at least approximately coincide with the vertical axis of the overall device 10, and which may be a prismatic direction of a central opening 310 through endplate 300. On the external surface 302, the endplate 300 may have one or more localized features such as teeth, rails, ridges, grooves, knurling or combinations thereof, for example on the external or bone-facing surface 302. Despite the possible presence of such localized features, the external surface 302 may be described by an enveloping external surface 304 that may coincide with repeated aspects of repeated features of the external surface 302. As illustrated, the enveloping external surface 304 may be a plane or slightly curved surface that is approximately perpendicular to the vertical axis of the endplate 300. However, if desired, the endplate 300 can include a lordosis or other angle defined between the enveloping external surface 304 and a plane that is perpendicular to the vertical axis.

As illustrated, the ridges or grooves can have a pitch (distance between corresponding repeated features) and can have a leading angle and a trailing angle. One of the angles, i.e., leading or trailing angles, can be from about 30° to about 90°, for example about 50°. The leading angle and the trailing angle can be unequal to each other so as to provide a preferred direction of sliding of the overall device 10 with respect to adjacent tissue such as vertebral surfaces.

The endplate 300 may have a central opening 310 therethrough. The shape and dimensions of the central opening 310 may be defined as the shape and dimensions, in a cross-section perpendicular to the prismatic axis of the prismatic solid, of the largest-cross-section prismatic solid that will fit through the central opening 310. This shape may be at least approximately a rectangle with rounded corners. The perimeter of the central opening 310 may meet the external surface 302 of the endplate 300 at an edge.

The endplate 300 may comprise a projection which may be referred to as a stability bar 370, which may depend away from the external surface 302 of the endplate 300. In the longitudinal direction, the stability bar 370 may occupy less than the full length of endplate 300. In a cross-section taken perpendicular to the vertical axis of the endplate 300, the stability bar 370 may have a cross-section that is generally rectangular, but which may include rounded corners. There may be a pair of stability bars 370, opposed to each other, one on each side of a centerplane of the endplate 300. The stability bars 370 may be symmetric or mirror-image with respect to each other. The stability bars 370 may have parallel surfaces facing each other internally, defining a distance therebetween in the lateral direction. The distance between the two stability bars 370 that face each other may be the same as the lateral dimension of the central opening 310 through the endplate 300 at the location of the stability bars 370.

The top endplate 300 can comprise, on a surface opposed to the external surface 302, a first endplate ramp 331 near one end of the endplate 300 and a second endplate ramp 332 near the opposite end of the endplate 300. The two ramps 331, 332 can face in the same direction as each other, and may be described as outward-facing as discussed elsewhere herein. The two ramps 331, 332 may have ramp angles as defined in FIG. 9E. The two ramps 331, 332 may be parallel to each other. There may further be additional ramp surfaces 331a, 331b, 332a, 332b, which may be parallel to each other or to ramps 331, 332. The bottom endplate 300 can have similar features as the top endplate 300.

Any or all of the ramps can extend at a ramp angle with respect to the longitudinal axis of device 10. The absolute value of the ramp angle can be from about 10° to about 75°, more narrowly from about 25° to about 60°, yet more narrowly from about 40° to about 50°.

The ramps may comprise features suitable to engage with other complementary features on other components. As illustrated, one of the ramps 331, 332 has an engagement feature that comprises a protrusion. The other of the ramps 331, 332 has an engagement feature that comprises a receiving shape. As illustrated, ramp 331 has the protrusion and ramp 332 has the receiver. As illustrated, one of the ramps has a T-shaped groove and the other ramp has a T-shaped projection. However, other designs are also possible. Various surfaces of geometries such as T-shaped geometries may be parallel to each other or perpendicular to each other. In connection with a T-shaped projection or a T-shaped receiver, there can be inward-facing surfaces also. Various such dimensions are defined in FIGS. 9A-9G. Dimensional interrelationships with dimensions of other components of device 10 are described elsewhere herein or may be as would be expected in order to permit the various parts to fit together.

In an embodiment of the invention, there may be provided an implantable device 10 having a central mechanism and an endplate 300, wherein the endplate 300 comprises a first outward-facing ramp (such as 331, 332) straddling both sides of a centerplane of the endplate 300, and further comprises further comprises a distinct separate outward-facing side ramp (such as ramps on 362, 364, 366 and 368) located so as not to intersect the centerplane of the endplate 300.

The various ramps, overhangs and other features as described may in combination provide, on the endplate 300, a first ramp surface (such as 331 or 332) and a second outward-facing ramp surface (such as 331 or 332), wherein the first ramp surface comprises a protrusion and the second ramp surface comprises a receiver.

The various ramps, overhangs and other features may be such that the implantable device 10 has a central mechanism and an endplate, wherein the endplate comprises a first outward-facing ramp surface that has an engagement feature (such as ramp 331 or 332) and a second outward-facing ramp surface that does not have an engagement feature (such as ramp surfaces 362, 364, 366, 368).

The various ramps overhangs and other features as described may in combination provide, on the endplate 300, a first outward-facing ramp surface (such as 331 or 332) and a second outward-facing ramp surface (such as 331 or 332) and a third outward-facing ramp surface (such as ramp surfaces 362, 364, 366, 368), wherein the first, second and third outward-facing ramp surfaces lie in different planes and are parallel to each other.

There can be four different outward-facing ramp surfaces, such as 362, 364, 366, 368, and also 331, 331*b*, 332, 332*b*. There can be three outward-facing non-coplanar ramp surfaces, which may be parallel to each other. There may be three non-coplanar ramp surfaces in any one side, in the longitudinal direction, from the proximal-distal midpoint.

The endplates 300 may comprise overhanging guides 372, 374, 376, 378. As illustrated, there are two overhanging guides 372, 374 on one side of endplate 300, and two more overhanging guides 376, 378 on the other side of endplate 300. When viewed from a lateral direction, the overhanging guides 372, 374, 376, 378 may have a generally trapezoidal shape, possibly with rounded corners. The sloped sides of the overhanging guides 372, 374, 376, 378 may have an angle that generally matches the angles of the ramps 362, 364 and of ramps 162, 164, 262, 264.

A ramp surface can have a slope direction, which may be defined such that the slope direction is contained in the ramp surface plane, and such that the slope direction and the longitudinal direction of the implantable device 10 can form an angle. With respect to the slope direction, a width can be defined as being measured in a direction perpendicular to the slope direction, and measuring the extent within which the ramp surface is truly planar, i.e., to a point at which the surface departs from planarity such as by a corner or a fillet etc. In the example as shown, it can be observed that there are various different widths for ramp surfaces 331, 331*a*, 331*b*, 332, 332*a*, 332*b*, and the width(s) of surface of ramps on features 362, 364, 366, 368. Similarly, other comparisons of ramp surfaces on the endplate 300 would also show unequal ramp widths. The various ramps, overhangs and other features as described may in combination provide, on the endplate 300, a first ramp surface (such as 331 or 332) and a second outward-facing ramp surface (such as 331 or 332), wherein the endplate comprises a first outward-facing ramp surface and a second outward-facing ramp surface, wherein the first and second ramp surfaces are of unequal widths.

The slope angle of any or all of ramps 131, 131*a*, 132, 132*a*, 132*b*, 162, 164 may generally equal the slope of ramps 331, 331*a*, 331*b*, 332, 332*a*, 332*b*, 362, 364, 366, 368.

With continued reference to FIGS. 9A-9G particularly FIG. 9G, it is possible that one of the ramps 331, 332 or its associated engagement features, or both, can intersect the external surface 302 of endplate 300 at an edge that is a part of the perimeter or edge where central hole 310 passes through the endplate 300, such through as the external surface 302 of endplate 300.

It is further possible that endplate 300 can have a recess such as semicylindrical recess 388, 389 that may accommodate a portion of the drive mechanism 400 or the guide mechanism 500.

The device may further comprise a gentle curve on the endplates and may have fillets or rounded corners in various places such as places that abut bodily tissue.

Dimensional and Design Interrelationships Involving the Endplates

Referring now to FIGS. 10A-10E, there may exist certain geometric relationships among the proximal ring structure 100, the distal ring structure 200, the urging structure 250 connected to or integral with distal ring structure 200, and the endplates 300 including the stability bars 370 that are connected to the endplates 300.

The ramp angle 341, 342 of the ramps 331, 332 of endplate 300 may equal the ramp angle 141, 142 of the ramps 131, 132 on the proximal ring structure 100. The device 10 can have an internal paired expansion sliding interface. The expansion sliding interface can include the ramp wedges slidably interfacing with complementary ramp surfaces of the endplates 300. The interface between the ramp wedges and the endplate wedges can include direct contact, such as a flat abutment, guides, rails, grooves, tracks, T-slots or combinations thereof. The various ramps and features such as protrusions or receivers may have local dimensions that enable them to fit with and interengage the ramps in the proximal ring structure 100 or other complementary shapes.

The vertical dimension of the urging structure 250 may be such that even at the maximum vertical expansion of the device 10, the urging structure 250 maintains contact with corresponding aspects of the endplate 300, i.e., the urging structure 250 may maintain contact with the interior of endplate central opening 310. The urging structure 250 may also maintain contact with stability bar 370. In particular, the shape and dimensions of urging structure transition region 252 may be such as to maintain such contact throughout a desired range of motion of the various components of device 10.

Referring now to FIGS. 10A-10E, there is illustrated a possible relationship, in the lateral direction, between the stability bars 370 and the proximal ring structure 100 and the distal ring structure 200. The laterally-outward-facing surface of the stability bars 370 may be closely-fitting with the inward-facing surface of the proximal ring structure 100 and the distal ring structure 200. Stated differently, the external lateral dimension between laterally opposed pairs of stability bars 370 can be such as to just fit inside the proximal ring structure 100 and the distal ring structure 200. This is illustrated in FIGS. 10A-10C, which shows a cross-sectional view for three different heights of the overall device (minimum, intermediate and maximum heights).

The stability bar 370 of the top endplate 300 can abut the stability bar 370 of the bottom endplate 300 when the device 10 is in a fully vertically contracted configuration. The lateral dimension of the urging structure 250, at its point most vertically distant from the midplane of the device 10 (the midplane being a plane perpendicular to the vertical direction), may be smaller than or approximately equal to the lateral dimension of the central opening 310 through endplate 300.

In the lateral direction, the urging structure 250 (particularly the portion of urging structure 250 farthest from the midplane of device 10) may have an external lateral dimension, which may be defined between parallel surfaces. This external lateral dimension of the vertically-outward-most part of urging structure 250 may be smaller than or approximately equal to the lateral dimension of the central opening 310 through endplate 300. The distal ring structure 200 may have a smallest internal width in a lateral direction. The external lateral dimension of the vertically-outward-most part of urging structure 250 may be smaller than the smallest internal width of the distal ring structure 200 in a lateral direction. The proximal ring structure 100 may have a smallest internal width in a lateral direction. The external lateral dimension of the vertically-outward-most part of urging structure 250 may be smaller than the smallest internal width of the proximal ring structure 100 in a lateral direction.

Upon actuation of the actuation mechanism 400 so as to cause vertical expansion of the overall device 10, the urging structure 250 may urge against an internal surface of opening 310 of the endplate 300 to cause endplate 300 to ride upward along the ramp structure 131, 132 and thereby cause expansion of the overall device 10 in the vertical direction. Upon actuation of the actuation mechanism 400 so as to cause contraction of the overall device 10, the urging structure 250 may urge against the stability bar 370 to cause endplate 300 to ride downward along the ramp structure 131, 132 (with the endplate 300 possibly also having interacting with the related ramp surfaces 131a, 132a) and thereby cause contraction of the overall device 10 in the vertical direction. In order to accomplish this, there may be an interrelation among the various parts such that the transition region 252 of urging structure 250 of distal ring structure 200 makes appropriate contact with stability bar 370. Such contact may serve to urge stability bar 370 and hence endplate 300 as a whole to move in a direction that would contract the vertical height of device 10. In general, urging structure 250 may, in a longitudinal direction, fit between stability bar 370 and an internal surface of central opening 310 of endplate 300.

As discussed, proximal ring structure 100 and distal ring structure 200 may have ramps 162, 164, 262, 264, which may be part of rounded-trapezoidal cutouts having a shape that is a portion of a trapezoid having rounded corners. The sloped surfaces of ramps 162, 164, 262, 264 may be substantially parallel to the sloped surfaces of overhanging guides guide 372, 374, 376, 378 of the endplates 300 that are located near them. There may be corresponding sloped features on an endplate 300 as described elsewhere herein. It is possible that at the maximally vertically contracted configuration of the device 10, the overhanging guides guide 372, 374, 376, 378 can bottom out against the ramps or cutouts 162, 164, 262, 264.

It is possible that at the maximally vertically contracted configuration of the device 10, a stability bar 370 from the upper endplate 300 can bottom out against the stability bar 370 from the lower endplate 300.

The inside width between the overhanging guides 362, 364 that are laterally opposite each other can be chosen to be approximately equal to the larger inside width of the appropriate one of the ring structures with which that overhanging guide interacts. The external width of the overhanging guides that are laterally opposite each other can be chosen to be approximately equal to the larger external width of the appropriate one of the ring structures with which that overhanging guide interacts. Both of these dimensional choices would help to align the respective ramp or bearing surfaces with each other for load transfer between the overhanging guides and the appropriate ring structure. The overhanging guides may slide on the corresponding slide ramps such as 162, 164 of the proximal ring structure 100 or side ramps 262, 264 of the distal ring structure 200.

The external width of the overhanging guides that are laterally opposite each other can be chosen to be substantially equal to the external width of the endplate 300 at that same location, which may also be at least approximately equal to the maximum external width PEW1 of the proximal ring structure 100 or the maximum external width DEW1 of the distal ring structure 200.

The slopes of the rounded-trapezoidal receiving cutout may have slopes that match the slopes of the angles of the sides of the trapezoidal overhanging guide 372, 374, 376, 378.

It is possible, as illustrated, that the endplate 300 may have both a stability bar 370 more internally and an overhanging guide 372, 374, 376, 378 more externally, with relatively internal and relatively external being defined in the lateral direction.

Referring now to FIG. 11 and FIG. 12, it is possible that the translational motion is driven by an actuation mechanism 400 and is guided by a guide mechanism 500 different from the actuation mechanism 400, with the actuation mechanism 400 being located at a first end of the device 10 and the guide mechanism 500 being located at a second opposed end of the device 10. The actuation mechanism 400 may have an actuation axis and the guide mechanism 500 may have a guide axis, and the actuation axis and the guide axis may be collinear with each other. The actuation mechanism 400 may be at the proximal end of the device 10, and the guide mechanism 500 may be at the distal end of the device 10.

An embodiment of the invention may comprise actuation mechanism 400 which may comprise drivescrew 450. As illustrated, the drivescrew 450 may have threaded engagement with hole 280 in distal ring structure 200. Accordingly, drivescrew 450 may have a threaded region 452 of drivescrew 450. As illustrated, drivescrew 450 may have a simple pass-through relationship (i.e., no thread engagement) with hole 180 in proximal ring structure 100, which may be achieved with drivescrew 450 having an unthreaded region 454 adjacent to its head 460, although other designs are possible also. Drivescrew 450 may have an enlarged head 460 that bears against recess 182 in proximal ring structure 100 to transmit force and serve as a stop against translational motion in one direction of drivescrew 450 relative to proximal ring structure 100. Thus, when drivescrew 450 is rotated in the appropriate direction, it may pull distal ring structure 200 in a translational manner toward proximal ring structure 100, or more specifically may pull first side 221 of distal ring structure 200 toward first side 121 of proximal ring structure 100. This may accomplish vertical expansion of the overall device 10. It is further possible that when drivescrew 450 is rotated in the appropriate opposite direction, drivescrew 450 may push first side 221 of distal ring structure 200 away from first side 121 of proximal ring structure 100. This may accomplish vertical contraction of the device 10. This motion may be assisted by the capture of snap-ring 490 in both groove 480 of drivescrew 450 and groove 196 of proximal ring structure 100. Such captured relationship may provide reaction force to prevent expulsion of the drivescrew 450 from proximal ring structure 100 during vertical contraction of the overall device 10.

Drivescrew 450 may additionally have a tool interface feature such as a non-circular socket, suitable to engage a feature of a tool and receive torque from the tool. Of course, other designs of drive mechanism 400 are also possible.

Referring now to FIG. 14D, an embodiment of the invention may further comprise a guide mechanism 500. Guide mechanism 500 may be located at the opposite end of the device, along the longitudinal direction, from the end where the actuation mechanism 400 is located. Guide mechanism 500 may comprise a guide pin 590 that may be fixedly attached to one of the ring structures 100, 200, and may be in slidable relationship with the other of the ring structures 100, 200. In such manner, translational motion is allowed between proximal ring structure 100 and distal ring structure 200 along the longitudinal direction, but constraint is provided against certain other forms of motion. More specifically, as illustrated, guide pin 590 is in slidable relationship with hole 190 in proximal ring structure 100. Also as illustrated, guide pin 590 is in fixed relationship with distal ring structure 200. As illustrated, guide pin 590 may be externally threaded and hole 290 in distal ring structure 200 may be internally threaded to accept the threads of guide pin 590. However, it is possible that the threadedness of hole 290 and the slidable relation of hole 190 could be reversed. It is also to be understood that other designs, such as press-fitted relationship or staked relationship, are also possible. It can also be noted that it is not essential for there to be any guide mechanism 500 at all.

It can be noted that the central opening 12 of the device 10 does not have a drivescrew or any other component crossing entirely across the central opening 12 in the longitudinal direction or any direction, and so central opening 12 can provide a relatively unobstructed path for the packing of bone growth promoting material in the central opening 12 and for the growth of bone through the central opening 12. This is true for the entire permitted range of positions of the proximal ring structure 100 relative to the distal ring structure 200, and for the entire permitted range of positions of upper endplate 300 relative to lower endplate 300. It is possible, depending on design details, that in some configurations there may be a modest projection of the actuation mechanism 400 into the central space, or a modest projection of the guide mechanism 500 into the central space, and in some configurations there may be no projection at all of one or the other of the actuation mechanism 400 and the guide mechanism 500. It can be seen that in any configuration, there is not a component that traverses all the way across the central opening 20 in the longitudinal direction or any direction. Although it should be understood that a component may traverse all the way across the central opening 20 in the longitudinal direction or any direction.

It is possible that, when the device 10 is in its minimum-height configuration, the urging structure 250 may extend less far in the vertically outward direction than the extreme ends of the teeth or similar features of the surface 302 endplate 300 extend in the vertically outward direction. It is possible that one surface of the urging structure 250 may have a slope that is approximately equal to one of the slopes of the grooves or ridges on the bone-facing surface of the endplate 300, i.e., the slope of the urging structure 250 may approximately equal either the slope of the leading edge or the slope of the trailing edge of the ridge or groove.

The interaction and force generation and motion generation between the proximal ring structure 100 and the driven ring structure may come from a drivescrew 450 that engages both the driving ring structure and the distal ring structure 200 without crossing the graft region in the forward-backward direction. The drivescrew 450 may be at the end of the assembly that is opposite the nose 115 of the assembly. The nose 115 may be a feature that is tapered, pointed or otherwise configured to push tissue out of its way to facility entry of the assembly into a surgical site.

Driving motion may be provided by a drivescrew 450 that is threadingly engaged with one ring structure and rotatably engaged with the other ring structure, both at a particular end of the assembly on a particular side of the graft window. Motion may be carried around the graft window space by the ring nature of the proximal ring structure 100 and distal ring structure 200. There may be a driven ramp and there may be a ring structure vertical extension that interacts with a feature of the endplate to urge the endplate ramp along the corresponding ramp in the driving ring structure.

Contracting of the assembly may also be driven by the drivescrew with the drivescrew being rotated in the direction of rotation opposite of the direction that caused expansion. Such rotation of the drivescrew may cause the vertical extension of the driven ring structure to push against a feature of the endplate to urge the endplate to slide along the ramps in a direction that results in contracture of the assembly in the intervertebral longitudinal direction.

Among the driving ring structure and the driven ring structure, all of the ramps that interact with an endplate may be located on one of the ring structures, which, for discussion purposes here, may be the driving ring structure. There may be two ramp interactions between the driving ring structure and any given endplate. One such ramp interaction may be closer to the forward end of the assembly and the other such interaction may be closer to the rearward end of the assembly. Both ramps may have engagement features which may be captured features such as a T-slot and a complementary shape, thereby allowing the endplate to be in a captured configuration with respect to the central mechanism. One of the ramp interactions may be such that the proximal ring structure 200 has the receiver while the endplate 300 has the protrusion. The other ramp interaction may be such that the proximal ring structure 200 has the protrusion and the endplate 300 has the receiver. As illustrated, a ramp with a receiver is on the proximal ring structure 200 close to the proximal end of the device 10. A ramp with a projection is on the proximal ring structure 200 towards the distal end of the device 10. Opposite features are on the endplate 300. As illustrated, the projection is a T-shape and the receiver is a T-shaped groove, although other geometries (either capturing or non-capturing) are possible.

Given that the assembly can both expand and contract, expansion may be driven by a vertical (or nearly vertical) surface of the urging structure 250 bearing against a vertical (or nearly vertical) surface of the endplate, which may be an internal surface of an opening 310 through endplate 300, and contraction may be driven by a vertical surface of the urging structure 250 bearing against a vertical surface of a stability bar 370. More generally, in this situation, "vertical" may mean a vertical or nearly-vertical surface.

The driven ring structure may comprise an urging structure 250, which may be driven by the drivescrew and may in turn interact with the endplate so as to urge the endplate to move in a horizontal direction with respect to the driving ring structure, thereby resulting in vertical motion of the endplate in view of the slope of the ramp. The urging structure 250 may be capable of interacting with the endplate in two different ways. One surface of the urging structure 250 may interact with a corresponding surface of the endplate such as an internal surface of an opening 310 through the endplate 300 so as to drive the endplate in expansion, and another surface of the urging structure 250 may interact with another corresponding surface of the endplate, in this case the stability bar 370, so as to drive the endplate in contraction. It may be appreciated that, in order that the endplate 300 and its stability bars 370 be able to translate vertically, the near-end wall thickness of the urging structure 250, in the longitudinal direction, may be equal to or just slightly less than the distance, in a longitudinal direction, between the vertical surface of the central opening 310 of endplate 300 and the nearby vertical surface of a stability bar 370.

A graft window may be defined at least in part by an end surface of the proximal ring structure 100, an end surface of the distal ring structure 200, and the inwardly-facing surfaces of the pair of stability bars 370 of each endplate 300.

It is possible that in the fully collapsed configuration, the ends of the stability bars 370 of one endplate 300 may touch the corresponding ends of the stability bars 370 of the other endplate 300.

It can be observed that there may be provided an implantable device 10 having a central mechanism comprising a first structure and a second structure able to undergo relative translation with respect to each other, with at least one of the structures having a driving ramp having an interlocking feature, and comprising an endplate 300 having an endplate ramp complementary to the driving ramp and to its interlocking feature, and comprising a drive means 400, wherein translation of the central mechanism in one direction drives the endplate 300 away from the central mechanism and translation of the central mechanism in the opposite direction drives the endplate 300 toward the central mechanism, and wherein the central mechanism has a central opening therethrough and the drive means 400 does not cross the central opening 12.

FIG. 12 illustrates that the drive means 400 may protrude to some extent into the central opening 12 of device 10, while still leaving most of central opening 12 unobstructed. It is possible that when device 10 is in a vertically expanded configuration, drive means 400 may protrude further into central opening 12 than is true for the vertically contracted configuration. It is possible that such increased protrusion of drive means 400 can help urge graft material to reconfigure itself and contact adjacent vertebrae.

FIGS. 13A-13B illustrate possible load paths when the device 10 is being expanded. FIGS. 13A-13B illustrate that redundant load paths may be provided. FIG. 13A is a section taken at the centerplane, and FIG. 13B is a section taken at a plane removed from the centerplane. As illustrated in the load path labeled load path 1, drivescrew 450 may interact with urging structure 250, which may be part of first side 221 of distal ring structure 200, to generate motion or load, which may be transmitted to and through urging structure 250 such that urging structure 250 contacts the facing surface of endplate 300 and thereby urges endplate 300 to slide along the appropriate ramp surfaces, of proximal ring structure 100. Such motion advances endplate 300 leftward (as illustrated) with respect to proximal ring structure 100, and thereby advances endplate 300 vertically away from proximal ring structure 100 and distal ring structure 200. Also present in the device 10 is another possible load path, labeled load path 2. In load path 2, load may be generated by the interaction of drivescrew 450 with distal ring structure 200 specifically first side 221 of distal ring structure 200, and that load may be transmitted along the length of distal ring structure 200 via sides 222, 224 to the (distal) third side 223 of distal ring structure 200, such that a distal urging surface of distal ring structure 200 contacts a distal surface of endplate 300 and urges endplate 300 to slide along appropriate ramp surfaces (131, 132) of proximal ring structure 100. Such motion also advances endplate 300 leftward (as illustrated) with respect to proximal ring structure 100, and thereby advances endplate 300 longitudinally. Thus, two separate instances or load paths for urging have just been described. It is possible that both of these load paths may be simultaneously active. However, it is also possible that depending on detailed dimensional and geometric relationships and tolerances, only one of these described load paths may be active. If only one of these load paths is active, it can be either of the described load paths, again depending on appropriate dimensions and tolerances.

FIGS. 13C-13D also illustrates possible load paths when the device 10 is being vertically contracted. FIG. 13C is a section taken at the centerplane, and FIG. 13D is a section taken at a plane removed from the centerplane. As illustrated in the load path labeled load path 3, drivescrew 450 may interact with urging structure 250, which may be part of distal ring structure 200, to generate motion or load, which may be transmitted to and through urging structure 250 such that urging structure 250 contacts the facing surface of stabilizing bar 370 and thereby urges endplate 300, specifically one or more of its ramps, to slide along the corresponding ramp surface of proximal ring structure 100. Such motion advances endplate 300 rightward (as illustrated) with respect to proximal ring structure 100, and thereby advances endplate 300 so as to vertically contract the device 10. The relevant dimensions of stabilizing bar 370 and urging structure 250 may be such that contact between stabilizing bar 370 and urging structure 250 is maintained over the desired range of motion.

It is further possible that proximal ring structure 100 and distal ring structure 200 and both the drive means 400 and the guide means 500 may have respective central holes therethrough along the longitudinal direction of the device 10. These holes may be suitable to receive therein a guidewire such as a K-wire (Kirschner wire).

Anti-Back-Out Features or Locking Features

Optionally, an embodiment of the invention may comprise a feature to resist, limit or prevent backout or disassembly in regard to the drivescrew. Such feature either may resist rotation of the drivescrew 450 in both directions of rotation, or may preferentially resist rotation of the drivescrew 450 in the direction that corresponds to decrease of height of the overall device 10.

Drivescrew 450 may comprise a threaded shaft that engages a corresponding thread in distal ring structure 200. Referring now to FIGS. 14A-14C, drivescrew 450 may comprise a deformable member 463, which may be or may comprise a polymer that is softer than the material of which the drivescrew 450 is made. (Drivescrew 450 may be made of metal such as titanium or a titanium alloy.) Deformable member 463 may be placed and dimensioned to bear against a corresponding feature of proximal ring structure 100 in such a way as to create friction and resist motion of the drivescrew 450 with respect to proximal ring structure 100. Such deformable member 463 may initially be oversized so that it occupies larger space than the remaining threads of drivescrew 450 and creates a slight interference with the complementary threads that drivescrew 450 engages in distal ring structure 200. This interference may result in friction that resists rotation of drivescrew 450 with respect to distal ring structure 200. The deformable member 463 also may have damping or vibration absorption properties. As illustrated, deformable member 463 is placed in a receiving feature that is a slot 462 that passes through the threaded shaft 452 of drivescrew 450, although other geometries are also possible for placement of deformable member 463 in drivescrew 450.

It is further possible that the head of drivescrew 450 may contain a drivescrew groove 480 suitable to receive a snap-ring 490. The drivescrew groove in the head of drivescrew 450 may be axisymmetric. When the snap-ring 490 is in an unstrained state and is assembled so as to overlap with drivescrew groove 480, part of snap-ring 490 may be contained within drivescrew groove 480 and some other part of snap-ring 490 may extend out beyond drivescrew groove 480.

Proximal ring structure 100 may contain a proximal ring structure groove 196 that is dimensioned suitably to receive a portion of snap-ring 490.

Snap-ring 490 may further comprise a rounded leading outer edge, and may comprise a relatively sharp-cornered trailing outer edge. Proximal ring structure 100 may comprise an entrance chamfer, and proximal ring structure groove may comprise at least some sharp corners. Such features have been described in U.S. Pat. Nos. 7,001,389 and 7,766,911 and 7,780,666 and 7,785,327, which are hereby incorporated by reference in their entirety.

It is possible that snap-ring 490 and deformable member 463 may be used together in the same drivescrew 450. Alternatively, it is possible that either one of them could be used separately.

It is possible that the thread on the drivescrew 450 could, in cross-section in a plane that contains the longitudinal axis of drivescrew 450, have a thread profile having a leading edge angle and a trailing edge angle that are different from each other. It is possible that the leading edge or the trailing edge could, in that same cross-section, be substantially perpendicular to the longitudinal axis of drivescrew 450.

It is possible that in an embodiment of the invention, there may be provided an implantable device having a central mechanism comprising a first structure and a second structure, wherein the first structure and the second structure are connected by a drive means comprising a drivescrew, wherein the drivescrew comprises a head groove and one of the structures comprises a circumferential internal groove, and further comprising a snap-ring that partially occupies the head groove and partially occupies the circumferential internal groove. The partial occupying of the head groove and partial occupies the circumferential internal groove may occur at an unstrained configuration of the snap-ring.

General Considerations

Proximal ring structure 100, distal ring structure 200 and generally most other components may be made of a biocompatible metal such as titanium or a titanium alloy. However, endplates 300 may be made of or may comprise a polymer such as polyetheretherketone (PEEK). Any components may have appropriate coatings or surface treatments. For example, outward-facing surfaces may have a coating or surface treatment to encourage bone ingrowth. Sliding surfaces may have a friction-reducing coating or surface treatment.

In regard to assembling the described device 10, it is possible that first the proximal ring structure 100 may be assembled together with the distal ring structure 200, together with connecting components such as drive mechanism 400 and guide mechanism 500 (if used). Then, the drive mechanism 400 can be used to configure the assembly in a configuration corresponding to maximum or nearly maximum vertical expansion of the device, if the endplates 300 were present. Then, the endplates 300 can be slid onto the corresponding ramps of proximal ring structure 100 or any other relevant structure. Then, the drive mechanism can be used to reconfigure the assembly to a less than fully vertically expanded configuration, or perhaps to a fully vertically contracted configuration such as may be used for insertion of the device into a patient.

A possible typical vertical dimension of the device 10 may be a vertical height of 8 mm in the vertically contracted configuration, and a vertical height of 12 mm in the vertically expanded configuration. This means that the upper endplate 300 would have the ability to move 2 mm away from the central mechanism compared to its closest position, and the lower endplate 300 would also have the ability to move 2 mm away from the central mechanism compared to its closest position. If the various ramps have a slope of 45 degrees, this means that there would have to be a corresponding 2 mm of horizontal motion of and endplate ramp with respect to a ramp on the proximal ring structure 100. For the described design, this also implies 2 mm of relative horizontal translation of the proximal ring structure 100 and the distal ring structure 200. For example, the device 10 could have an overall length in the longitudinal direction of 24 mm when vertically contracted, and an overall length in the longitudinal direction of 22 mm when vertically expanded. Of course, devices having other dimensions are possible, and providing a set or kit containing various sizes of devices is also possible.

FIG. 15A is a three-dimensional illustration of two devices of an embodiment of the invention, placed in an intervertebral disc space, viewed from the anterior, with one vertebra shown semi-transparent, and with the intervertebral disc omitted for clarity of illustration.

FIG. 15B is a three-dimensional illustration of two devices of an embodiment of the invention, placed in an intervertebral disc space, viewed from the posterior, with one vertebra and the intervertebral disc omitted for clarity of illustration.

FIG. 15C is similar to FIG. 15B, with one vertebra and the intervertebral disc omitted for clarity of illustration, but with only one device shown, and further showing a portion of an implantation instrument.

During surgery, the device 10 may be introduced into the patient's body in a vertically contracted configuration and then may be reconfigured to a vertically expanded configuration. At some appropriate time the central opening 12 may be packed with bone growth promoting material as known in the art.

It is also possible that an embodiment of the invention could have endplates 300 that have only one overhang per side, rather than two overhangs per side as has been illustrated. The overhangs in such an embodiment still may have ramps as described, that interact with ramps on proximal ring structure 100 or distal ring structure 200 or both.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

All documents referred to herein are incorporated by reference in their entirety. The following US publications are incorporated by reference in their entirety: 20100211176; 20100222884; 20070219634.

We claim:

1. A spinal interbody device comprising:
a proximal ring structure having a proximal ring structure opening therethrough, said proximal ring structure opening having a proximal ring structure opening direction;
a distal ring structure having a distal ring structure opening therethrough;
an actuation mechanism suitable to cause relative motion between said proximal ring structure and said distal ring structure along a longitudinal axis, said relative motion including at least relative translation along a first motion direction along said longitudinal axis,
wherein, at any permitted relative position of said proximal ring structure and said distal ring structure, when viewed along said proximal ring structure opening direction, said proximal ring structure opening and said distal ring structure opening partially but not completely overlap with each other;
a first endplate and a second endplate, wherein said first endplate and said second endplate are opposed to each other and are suitable to bear against respective vertebrae;
wherein said relative motion between said proximal ring structure and said distal ring structure causes at least one of said first endplate and said second endplate to move toward or away from said proximal ring structure or said distal ring structure in a second motion direction different from said first motion direction;
wherein said proximal ring structure includes a first end and a second end, wherein said proximal ring structure opening decreases in width along said longitudinal axis from said first end towards said second end;
wherein said distal ring structure includes a first end and a second end, wherein said distal ring structure opening decreases in width along said longitudinal axis from said first end towards said second end; and wherein there is a sequence progressing along said longitudinal axis of said first end of said distal ring structure followed by said second end of said proximal ring structure followed by said second end of said distal ring structure followed by said first end of said proximal ring structure.

2. The spinal body implant of claim 1, wherein a first external width of said first end of each said proximal ring structure and said distal ring structure is larger than a second external width of said second end of each said proximal ring structure and said distal ring structure.

3. The spinal body implant of claim 1, wherein said actuation mechanism connects said second end of said distal ring structure to said first end of said proximal ring structure.

4. An implantable device comprising:
a proximal ring structure having a proximal ring structure opening therethrough and a first end and an opposing second end;
a distal ring structure having a distal ring structure opening therethrough and a first end and an opposing second end, wherein said distal ring structure being in movable relation to said proximal ring structure, said movable relation including at least translation in a first direction along a longitudinal axis;
wherein said proximal ring structure and said distal ring structure define an open region therethrough perpendicular to said first direction;
a first endplate, said first endplate having a face suitable to bear against a vertebra, said face having a central opening therethrough in communication with said open region;
said device includes a proximal end and an opposing distal end, wherein said open region is between said proximal end and said opposing distal end, wherein said device proximal end includes said proximal ring structure first end and said distal ring structure second end and said device distal end includes said proximal ring structure second end and said distal ring structure first end;
an actuation mechanism connecting said proximal ring structure first end to said distal ring structure second end, wherein said translation of said proximal ring structure relative to said distal ring structure in said first direction causes motion of said first endplate away from said proximal ring structure, and translation of said proximal ring structure relative to said distal ring structure in a second direction opposed to said first direction causes said first endplate to move toward said proximal ring structure; and
wherein said open region increases in length along said longitudinal axis when said translation of said proximal ring structure relative to said distal ring structure in said first direction causes motion of said first endplate away from said proximal ring structure.

5. The implantable device of claim 4, wherein said actuation mechanism does not cross said open region into said proximal ring structure second end and said distal ring structure first end.

6. The implantable device of claim 4, wherein said open region decreases in length along said longitudinal axis when said translation of said proximal ring structure relative to said distal ring structure in said second direction opposed to said first direction causes said first endplate to move toward said proximal ring structure.

7. The implantable device of claim 4, wherein there is a sequence progressing along said longitudinal axis of said first end of said distal ring structure followed by said second end of said proximal ring structure followed by said open region followed by said second end of said distal ring structure followed by said first end of said proximal ring structure.

8. The implantable device of claim 4, further comprising a second endplate, wherein said first endplate and said second endplate are opposed to each other and each are suitable to bear against respective vertebrae.

9. A surgical kit comprising:
at least one spinal interbody device, comprising:
a proximal ring structure having a proximal ring structure opening therethrough, said proximal ring structure opening having a proximal ring structure opening direction;
a distal ring structure having a distal ring structure opening therethrough;
an actuation mechanism suitable to cause relative motion between said proximal ring structure and said distal ring structure along a longitudinal axis, said relative motion including at least relative translation along a first motion direction along said longitudinal axis,
wherein, at any permitted relative position of said proximal ring structure and said distal ring structure, when viewed along said proximal ring structure opening direction, said proximal ring structure opening and said distal ring structure opening partially but not completely overlap with each other;
a first endplate and a second endplate, wherein said first endplate and said second endplate are opposed to each other and are suitable to bear against respective vertebrae;
wherein said relative motion between said proximal ring structure and said distal ring structure causes at least one of said first and second endplates to move toward or away from said proximal ring structure or said distal ring structure in a second motion direction different from said first motion direction, and
wherein said device has a central opening therethrough generally along a vertical direction, said central opening being bounded in sequence around its perimeter by a first end, a first side, a second end and a second side, wherein in said sequence, said central opening is bounded on said first end by said proximal ring structure; then, on said first side adjacent to said first end, said central opening is bounded first by said proximal ring structure and then is bounded by said distal ring structure; then, on said second end, said central opening is bounded by said distal ring structure; then, on said second side, said central opening is bounded first by said distal ring structure and then by said proximal ring structure.

10. The surgical kit of claim 9, further comprising a surgical instrument to grasp said at least one spinal interbody device.

11. The surgical kit of claim 9, further comprising a second spinal interbody device different in dimension from said at least one spinal interbody device.

12. The surgical kit of claim 9, wherein said central opening may be packed with bone growth.

13. An implantable device comprising:
a proximal ring structure having a proximal ring structure opening therethrough and a first end and an opposing second end;
a distal ring structure having a distal ring structure opening therethrough and a first end and an opposing second end, wherein said distal ring structure is in movable relation to said proximal ring structure, said movable relation including at least translation in a first direction along a longitudinal axis;

wherein said proximal ring structure and said distal ring structure define an open region therethrough perpendicular to said first direction;

a first endplate, said first endplate having a face suitable to bear against a vertebra, said face having a central opening therethrough in communication with said open region;

said device includes a proximal end and an opposing distal end, wherein said open region is between said proximal end and said opposing distal end, wherein said device proximal end includes said proximal ring structure first end and said distal ring structure second end and said device distal end includes said proximal ring structure second end and said distal ring structure first end;

an actuation mechanism connecting said proximal ring structure first end to said distal ring structure second end, wherein said translation of said proximal ring structure relative to said distal ring structure in said first direction causes motion of said first endplate away from said proximal ring structure, and translation of said proximal ring structure relative to said distal ring structure in a second direction opposed to said first direction causes said first endplate to move toward said proximal ring structure; and wherein there is a sequence progressing along said longitudinal axis of said first end of said distal ring structure followed by said second end of said proximal ring structure followed by said open region followed by said second end of said distal ring structure followed by said first end of said proximal ring structure.

14. The implantable device of claim 13, wherein said actuation mechanism does not cross said open region into said proximal ring structure second end and said distal ring structure first end.

15. The implantable device of claim 13, wherein said open region increases in length along said longitudinal axis when said translation of said proximal ring structure relative to said distal ring structure in said first direction causes motion of said first endplate away from said proximal ring structure, and wherein said open region decreases in length along said longitudinal axis when said translation of said proximal ring structure relative to said distal ring structure in said second direction opposed to said first direction causes said first endplate to move toward said proximal ring structure.

16. The implantable device of claim 13, further comprising a second endplate, wherein said first endplate and said second endplate are opposed to each other and each are suitable to bear against respective vertebrae.

* * * * *